US012766181B2

(12) United States Patent
Rahimi

(10) Patent No.: US 12,766,181 B2
(45) Date of Patent: Oct. 20, 2026

(54) ORAL CARE PRODUCTS

(71) Applicant: Maryam Rahimi, Long Beach, CA (US)

(72) Inventor: Maryam Rahimi, Long Beach, CA (US)

( * ) Notice: Subject to any disclaimer, the term of this patent is extended or adjusted under 35 U.S.C. 154(b) by 480 days.

(21) Appl. No.: 18/412,569

(22) Filed: Jan. 14, 2024

(65) Prior Publication Data

US 2024/0189378 A1 Jun. 13, 2024

Related U.S. Application Data

(63) Continuation of application No. 16/693,356, filed on Nov. 24, 2019, now Pat. No. 11,872,258.

(51) Int. Cl.

| | |
|---|---|
| ***A61K 36/73*** | (2006.01) |
| ***A61C 15/04*** | (2006.01) |
| ***A61K 9/00*** | (2006.01) |
| ***A61K 9/1273*** | (2025.01) |
| ***A61K 9/16*** | (2006.01) |
| ***A61K 9/50*** | (2006.01) |
| ***A61K 36/45*** | (2006.01) |
| ***A61K 36/898*** | (2006.01) |
| ***A61M 11/04*** | (2006.01) |
| ***A61M 15/06*** | (2006.01) |
| ***A61P 11/00*** | (2006.01) |
| ***A61P 35/00*** | (2006.01) |
| ***C12N 5/04*** | (2006.01) |

(52) U.S. Cl.

CPC ............ *A61K 36/73* (2013.01); *A61K 9/0056* (2013.01); *A61K 9/006* (2013.01); *A61K 9/0073* (2013.01); *A61K 9/1273* (2013.01); *A61K 9/1647* (2013.01); *A61K 9/1652* (2013.01); *A61K 9/5026* (2013.01); *A61K 9/5036* (2013.01); *A61K 36/45* (2013.01); *A61K 36/898* (2013.01); *A61M 11/04* (2013.01); *A61M 15/06* (2013.01); *A61P 11/00* (2018.01); *A61P 35/00* (2018.01); *C12N 5/04* (2013.01); *A61C 15/046* (2013.01)

(58) Field of Classification Search

CPC ........ A61K 36/87; A61K 36/03; A61K 36/04; A61K 36/14; A61K 36/235; A61K 36/28; A61K 36/45; A61K 36/48; A61K 36/534; A61K 36/61; A61K 36/708; A61K 36/73; A61K 36/74; A61K 36/82; A61K 36/84; A61K 36/85; A61K 8/97; A61K 2236/30; A61K 2236/51; A61K 2300/00; A23L 33/105; A23L 33/127; A61P 31/04; A61P 31/10; A23V 2200/30; A23V 2250/21; Y02A 50/30

See application file for complete search history.

(56) References Cited

FOREIGN PATENT DOCUMENTS

| | | | | |
|---|---|---|---|---|
| CN | 107510098 A | * 12/2017 | ........... | C12N 5/0665 |

OTHER PUBLICATIONS

CN-107510098-A, machine translation, abstract only (Year: 2017).*

* cited by examiner

*Primary Examiner* — Aaron J Kosar

(57) ABSTRACT

Embodiments of the invention include a system having a plant stem cell product and a delivery device configured to deliver an effective amount of the plant stem cell product to the oral cavity or nasopharynx. In some embodiments, the delivery device may include an aerosolizing device, an adherent dressing, a tooth-adherent flexible strip, a treatment tray, a viscous adherent carrier, a brush, a paste, a flosser, a dissolving oral strip, a gum, a chew, a smoking material, a nasal packing, or a lozenge. The plant stem cell products may include encapsulated extracts of plant stem cells, such as food species stem cells, spice or other seasoning stem cells, or medicinal plant stem cells.

17 Claims, 10 Drawing Sheets

Acridine Orange/Ethidium Bromide Staining of Lung Cancer Cell Line A549

Acridine Orange/Ethidium Bromide Staining of Lung Cancer Cell Line NCI-H520

Calcein AM Staining in A549 Lung Cancer Cell Line

Calcein AM Staining in NCI-H520 Lung Cancer Cell Line

ORAL CARE PRODUCTS

RELATED PATENT APPLICATION

This application is a continuation of U.S. application Ser. No. 16/693,356 filed Nov. 24, 2019 by Maryam Rahimi, which claims the benefit of U.S. provisional patent application No. 62/776,237 entitled aerosol treatments, filed on Dec. 6, 2018 by Maryam Rahimi. The entire content of the parent application and of the provisional patent application are incorporated herein by reference for all purposes.

REFERENCE TO A SEQUENCE LISTING SUBMITTED VIA EFS-WEB

The content of the ASCII text file of the sequence listing named "MR03_ ST25.txt", which is 354 bytes in size was created on Nov. 24, 2019 and electronically submitted via EFS-Web is incorporated herein by reference in its entirety.

Title: Oral Cavity Treatments

Inventor: Maryam Rahimi

TECHNICAL FIELD

This invention relates to treatment of conditions by application of plant stem cell products. In embodiments, the invention includes treatment of oral cavity and nasopharyngeal conditions by application of compositions including plant stem cell products.

BACKGROUND

Plant extracts form the basis of most traditional medical treatments. Active materials isolated from plant extracts, ranging from aspirin to morphine to paclitaxel to quinine form a large fraction of the modern pharmacopeia. The structural diversity of plant-derived compounds is enormous, and its exploration is still an active part of pharmaceutical development. Plants are the source of numerous compounds of therapeutic value in human disease. The major classes of plant-based medicines include alkaloids, glycosides, polyphenols, and terpenes.

Multicellular plants, like animals, are composed of differentiated tissues and stem cells. Plant stem cells are dedifferentiated cells capable of division to create more stem cells and differentiated cells or their precursors. These replicating cells may be isolated from a part of a plant regenerating from an injury or the progeny of such cells. Injury sites may be from any portion of a plant such as callus, leaves, fruit, stems, flowers, roots, meristem, root cap, or seeds. Other plant stem cells may be derived from cells of a developing plant embryo, from a plant callus, or from plant tissue samples (explants) in tissue culture medium in vitro. Plant stem cells may be derived from many different cell types and may be able to differentiate into a whole plant. Plant stem cells, as used in this document, includes at least meristem cells, callus-derived cells, injury-site derived cells, and embryonic cells. Meristem cells at ends of stalks and in the root apex provide the plant with new cells and enable the plant to grow throughout its life. A callus is a stage of somatic embryogenesis (i.e. zygote formation without fertilization) followed by dedifferentiation producing stem cells capable of generating new plant tissue.

Differentiated plant cells produce a wealth of compounds evolved to combat predation, parasitism, disease, or adverse climatic conditions, to signal, or to encourage pollination or seed distribution. Differentiated plant cells such as roots, flowers, fruit, and seeds produce many of these compounds. However, plant stem cells by their nature lack the more specialized synthetic apparatus of differentiated cells. Instead, plant stem cells would be expected to focus more narrowly on producing materials needed to establish or replace other cell types, leaving the more diverse chemical synthesis tasks to specialized progeny. For example, plant stem cells in sprouting seeds, such as the germinated barley used in brewing, direct much enzymatic activity to producing simple sugars (such as the disaccharide maltose) to support the energy needs of a growing embryo.

Plant stem cells also have properties and functions that help stimulate and regenerate plants after injury and stress. This is most evident in the recovery from physical injuries such as in a wound or callus.

As in other eukaryotes including mammals, plant cells include telomeres that limit somatic cell division. Telomeres are ribonucleoprotein structures capping the ends of chromosomes. Telomeres shorten with each cell division, but telomerase, a reverse transcriptase, elongates telomeres in stem cells. Telomerase expression profiles mirror changes in telomere length, with the highest enzyme levels and telomere lengths associated with cells that have unlimited capacity for proliferation. Cells with reduced length telomeres undergo senescence or apoptosis. In large-bodied or long-lived animals, this process protects against somatic cell-derived cancers.

In vertebrates, telomeres are composed of 6-mer TTAGGG repeats coated with specific protecting proteins. Most plant telomeres (including model organism *Arabidopsis thaliana*) contain the 7-mer TTTAGGG that includes the vertebrate 6-mer. The *Arabidopsis*-type telomere is found in most angiosperms, but the sequence is absent in most monocot Asparagales species. Many species within Asparagales include the 6-mer TTAGGG sequence found in humans. Apparently, this sequence was altered during the rise of the Asparagales, an order including more than ten percent of all angiosperms. Onions (*Allium cepa*) are members of Asparagales and include the 12-mer telomere sequence CTCGGTTATGGG (SEQ ID NO:1), which also includes the human 6-mer sequence.

Human tissue may be afflicted with a variety of diseases and conditions, such as injury, wounds, infection, inflammation, infarct, cancer, or diseases unique to specialized tissues. In some cases, these conditions may be treated by systemic administration of medications, including plant-derived medications. In other cases, these conditions may be treated by local administration of therapeutic agents to avoid unwanted effects outside the treated tissue or to limit the overall dosage.

The human (or other mammalian) oral cavity includes a variety of tissue types, making up several anatomical structures. These include at least oral mucosa, gums, teeth, hard palate, soft palate, salivary ducts, tonsils, epiglottis, uvula, inner aspect of the lips, and tongue. The oral cavity is a wet environment under frequent mechanical stress from biting, chewing, sucking, swallowing, and worrying by the tongue. It is subject to a variety of insults including microbial growth, mechanical action, heat, cold, tobacco smoke, alcohol, hypo and hyper osmotic conditions, a wide range of pH, chemical action, and a combination of any or all of these. These insults and other body conditions may produce abrasions, infected sores, cuts, burns, inflammation, infections, oral cancers, erosive lesions, and tooth decay. Some oral cavity conditions may be treated by direct topical administration of medications through the mouth. In some cases, plant-based materials may treat some of these conditions.

There is a need to treat conditions of the oral cavity using medically effective plant-based materials that withstand the physiochemical environment of the mouth long enough to provide effective treatment.

The nasopharynx has some similarities to environmental conditions to the oral cavity. The nasopharynx includes a mixture of tissues making up the structures of the nasal cavity including the nostrils, septum, turbinates, pharyngeal tonsils and Eustachian tubes. Nasal mucosa is subject to movement of air and of mucus; breathing, sneezing, coughing, and forcible sniffing and nose blowing can create high velocity movement of nasal contents. Rhinitis can flood the nasal cavity with mucus of different viscosities. Dried nasal mucus can entrap materials and may be violently expelled. There is also a need to treat conditions of the nasopharynx using medically effective plant-based materials that withstand the physiochemical environment of the nose long enough to provide effective treatment.

The "hostile environment" inside the mouth and nose interferes with topical administration of many medications. While some solid medicines can be rapidly absorbed through relatively thin portions of the oral mucosa into the systemic circulation, many liquid medications intended for topical application are quickly rinsed, diluted, or scoured away by normal oral cavity or nasal action. There is a need to provide topical medications to portions the oral cavity that resists dispersal due to normal oral cavity action.

Portions of the oral cavity are difficult to reach for effective administration of medications because of the interference of nearby structures. This occurs most frequently around the teeth which may abut one another very closely. Portions of the gingival mucosa may shield parts of the teeth. Dental pulp is usually shielded by dental enamel. Portions of the oral mucosa, gingiva, teeth and lips may be intermittently shielded by the tongue. There is thus a need to provide more effective administration of treatment materials to the oral cavity.

The effectiveness of any treatment requires the delivery of the treatment agent to the treatment site. This is simple in the case of open wounds giving direct access but may be much more difficult when tissue intervenes between the treatment site and the most convenient available access location. As affected area may be in any location, it is useful to have a variety of delivery devices to effectively reach this variety of locations. There is thus a need to provide a variety of delivery devices to treat disorders of the oral cavity and nasopharynx.

Systemic administration of medications may not be optimal to treat oral cavity or other body conditions. For example, plants of the genus Ephedra, including *E. sinica* and others, produce the alkaloids ephedrine and pseudoephedrine in at least their stems and leaves. However, when taken systemically, extracts of Ephedra species have been associated with adverse cardiovascular and renal events and with anxiety, dizziness, difficulty urinating, dry mouth, headache, irritation of the stomach, nausea, psychosis, restlessness, sleep problems, and tremors. The FDA banned the U.S. sale of dietary supplements containing ephedrine alkaloids, as posing an unreasonable risk of injury or illness. Thus, systemically administered materials may have off-target effects that limit their use.

Flavonoids are polyphenolic compounds (a subclass of flavanols) in plant-based foods. Quercetin, a strong antioxidant, is the major food flavonoid. Quercetin can chelate metals, scavenge oxygen free radicals and prevent the oxidation of low-density lipoprotein (LDL). Oxidized LDL is an intermediate in the formation of atherosclerotic plaques. Quercetin might therefore contribute to the prevention of atherosclerosis: the intake of flavanols is inversely associated with subsequent cardiovascular disease in several prospective epidemiological studies. Epidemiological studies suggest that consumption of quercetin protects against cardiovascular disease, but its absorption in man is controversial. Feeding studies of plant-based foods in humans found quercetins from foods such as onions, which contain glucose conjugates of quercetin, were more readily absorbed than non-conjugated quercetins from apples or tea. Bioavailability of quercetin was about three times higher when the source contained glucose conjugates of quercetin. See Hollman et al. FEBS Lett. 1997 Nov. 24; 418(1-2): 152-6. There is a need to reach the end organ—the actual site of the condition. The site of treatment that is closest to the site of the affected tissue gives the highest chance of benefit. Thus, systemically administered materials may have limited bioavailability.

Different body conditions may be subject to different treatment efficacies even with the same method of administration. Lung conditions may be treated by aerosol inhalation as this may bring the treatment into direct contact with the affected tissue. The process of breathing delivers gases and inhaled materials directly to lung tissue, but the therapeutic effect of aerosolized therapies is dependent upon the dose deposited and its distribution. A drug or other treatment must be deposited past the oropharyngeal region to achieve therapeutic effectiveness in the lungs. The location of aerosol deposition, central or peripheral airways or alveolar, and the uniformity of distribution of the inhaled treatment may also play a role in the treatment's effectiveness.

Effectiveness of therapy may be compromised if an aerosol is delivered to a part of the lung devoid of the targeted disease or receptor. For example, autoradiographic studies have shown that receptors for the $\beta_2$ agonist albuterol are not uniformly distributed throughout the lung. These receptors are present in high density in the airway epithelium from the large bronchi to the terminal bronchioles. Airway smooth muscle has a lower $\beta_2$ receptor density, greater in the bronchioles than bronchi. However, more than 90% of all $\beta_2$ receptors are located in the alveolar wall, a region where no smooth muscle exists and whose functional significance is unknown.

Inhaled anti-inflammatory therapy is probably most beneficial when evenly distributed throughout the lung, since inflammatory cells, such as eosinophils, lymphocytes, macrophages, and dendritic cells, are present throughout the airways and the alveolar tissue in asthma.

It is an object of the invention to provide improved treatment systems and methods for disease states and conditions including oral cavity, nasopharyngeal, respiratory tree, lung, and other body conditions.

DISCLOSURE OF INVENTION/SUMMARY

This invention includes treatment devices and methods for treating conditions of the body, including the oral cavity and the nasopharynx. The treatment devices comprise delivery devices that include plant stem cell extracts. I have discovered that plant stem cell extracts can be applied to human tissues to enhance regeneration, to prevent oxidative damage, and to selectively kill cancer cells with relative sparing of normal cells.

In embodiments, the invention includes a system for treating a tissue of the body where the system includes a plant stem cell product ("plant SC product") and a delivery device. Delivery devices include mechanical applicators, vehicle compositions, or a combination of a mechanical applicator and a vehicle composition.

Mechanical applicators include any of a variety of devices that deliver plant stem cell extracts to some or all of the oral cavity. Among these devices are aerosolizing devices, adherent dressings, polymer tooth-adherent flexible strips, treatment trays, viscous adherent carriers, brushes, and flossers. Vehicle composition include pastes, gums, chews, lozenges, oral rinses, and dissolving oral strips.

A mechanical applicator may also include an injection device, a topical applicator, an eyedrop applicator, or an eardrop applicator. An injection device may comprise a syringe and hollow needle sized for subcutaneous injection, for intradermal injection, for intramuscular injection, for intravenous injection, for intracapsular injection, intraarticular injection, for intraosseous injection, for intraperitoneal injection, for intracavernous injection, or for cardiac injection. Such devices may treat conditions anywhere in the body; their use is not restricted to the mouth or nose.

In some embodiments, the invention includes a system for treating an oral or a nasal condition, where the system includes a plant stem cell extract and an aerosolizing device. The device is configured to create an aerosol from the plant stem cell product and to deliver the aerosol to the lung or to an affected area of the oral cavity or to the nose via inhalation. The aerosolizing device includes one or more of a nebulizer, pressurized metered-dose inhaler, a personal vaporizer, or an electronic-cigarette.

The delivery device may include a smoking material with the plant stem cell product applied to the smoking material.

The adherent dressing may include a substantially planar flexible patch that conforms to and sticks to the surface of oral mucosa. The tooth-adherent flexible strip may include a substantially planar flexible patch that conforms to and sticks to the surface of a tooth.

In embodiments, the treatment area may be one or more of a dental cavity, a pocket between a tooth and a receded gum, a space between closely spaced teeth, or a socket of a pulled tooth; the viscous adherent carrier delivery device may include a viscosity sufficient to retain an aliquot in the treatment area. The viscous adherent carrier may include one or more of a gelatin, an alginate, a food gum, or a hydroxy methylcellulose. In such embodiments, the plant stem cell products may be encapsulated.

The brush may include a bristle with the plant stem cell product affixed to the bristle. In such embodiments, the plant SC product may be encapsulated with the capsules adhered to the bristles.

In other embodiments, the paste includes an abrasive and a humectant admixed with the plant stem cell product.

In embodiments, the flosser includes a fiber, and the plant stem cell product is absorbed by or mechanically trapped by the fiber.

In other embodiments, the plant stem cell product may be encapsulated in a gelatin, powder, liquid, liposome, or other vehicle, and the oral rinse suspends the encapsulated plant stem cell product. Alternatively, the plant stem cell product may be encapsulated in a synthetic polymer, and the oral rinse may contain a solvent capable of softening the synthetic polymer.

The invention also includes a method of treating a condition at a treatment site in oral cavity of a mammal. the method has steps of providing a plant stem cell product, providing a delivery device to deliver the stem cell product to the oral cavity, and delivering the plant stem cell product via the delivery device through the mouth into the oral cavity.

In the method the plant stem cell product may include one or more of a plant stem cell extract, a lyophilized plant stem cell, a plant stem cell enriched medium, or an intact plant stem cell. The delivery device of the method may include one or more of an aerosolizing device, an adherent dressing, a tooth-adherent flexible strip, a treatment tray, a viscous adherent carrier, a brush, a paste, a flosser, a gum, a chew, a lozenge, a dissolving oral strip, and an oral rinse.

The plant stem cell product of the invention may include one or more of a plant stem cell extract, a lyophilized plant stem cell, or an intact plant stem cell. The plant stem cell may also include an excipient, such as lactose, mannose, sodium chloride, poly lactic acid, poly(lactic-co-glycolic acid), glycerol, a glycol, a surfactant, or a liposome.

The plant stem cell product may be encapsulated. The plant stem cell product is encapsulated in a capsule that comprises a polymer or a liposome.

While many plant types may be suitable for the invention, in some embodiments, the plant stem cell may be selected from species in a group consisting of vascular plants such as ferns, conifers, and angiosperms. In some embodiments, suitable species may be selected from plants with an extensive history of safe human consumption. Especially suitable may be fruit-bearing angiosperms such as apple, grape, lingonberry, mulberry, plantain, peppers (including *piper longum*), and other fruit species. Other suitable species include those of seasoning herbs or spices such as turmeric, poppy, ginger, garlic, thyme, oregano, mint, licorice root, sage, and other herb and spice species. Other suitable species have long formed a part of the human pharmacopeia, including *adhatoda vasica*, poppy, rose, hibiscus, *cannabis*, coltsfoot, elecampane, *eucalyptus, boswellia serrata* (frankincense), *ginseng*, hemp, *lebbeck*, lithy tree, licorice root, mullein, and other medicinal species. Some plants may be members of more than one of these groups. Suitable plant stem cells may also be selected from a group including apple, lithy tree, rose, hibiscus, mulberry, *cannabis*, hemp, *chrysanthemum, ginseng*, garlic, mint, grape, *eucalyptus*, lingonberry, lungwort, oregano, plantain, poppy, elecampane, *lobelia*, orchid, osha root, *Curcuma longa* (turmeric), ginger, sage, mullein, licorice root, coltsfoot, thyme, *adhatoda vasica, albizzia lebbeck, boswellia serrata, ocimum sanctum*, and *piper longum*. Embodiments of the invention may expressly include any subsets or combinations of the above described species, cultivars, or taxa, optionally excluding any species either listed, unlisted, or within the taxonomic groups listed.

The plant stem cell may include an apple stem cell.

The plant stem cell stem cell may be from an Asparagales species or from a species that has in its telomeres the repeated 6-mer sequence TTAGGG. The telomere may include a plurality of contiguous copies of the TTAGGG sequence. The plant stem cell may be derived from a monocot Asparagales species.

In other embodiments, the plant stem cell may have in its telomeres the repeated 12-mer sequence CTCGGTTATGGG (SEQ ID NO:1).

The applicator device may be an systemizing device, and may include one or more of a nebulizer, a pressurized metered-dose inhaler, a personal vaporizer, or an electronic-cigarette.

In other embodiments, the invention includes a method of treating an oral cavity, nasopharyngeal, or respiratory condition. The method includes steps of providing a plant stem cell product, providing a delivery device, and delivering the plant stem cell product via the delivery device. The plant stem cell product may be delivered such that at least 30% of the plant stem cell reaches a targeted treatment site.

The method may have a delivery device that includes one or more of an aerosolizing device, a smoking material, an adherent dressing, a tooth-adherent flexible strip, a treatment tray, a viscous adherent carrier, a brush, a paste, a flosser, a lozenge, a chew, a gum, a dissolving oral strip or an oral rinse.

The smoking material may be a smoking paper wrapped around another smoking material including herbs such as tobacco or *cannabis*; the step of delivering the plant stem cell product may include combusting or heating the herb or the smoking paper and inhaling smoke or vapor produced by the combustion or heating.

The targeted treatment site may include any part of the body. In embodiments configured for the oral cavity, the treatment site may be one or more of a tooth, a tongue, an oral mucosa, a gum, a tumor, or an ulcer, lesion, abscess, or erosive lesion within the oral cavity. In embodiments configured for the respiratory system, the treatment site may be a bronchus, a bronchiole, an alveolus, a lung parenchyma, or a capillary bed. The particle size distribution may include more than 50% of particles less than about 5 μm. In other embodiments, the particle size distribution may include a range of about 0.5 μm to about 5 μm where the treatment site includes a bronchus or a bronchiole. The particle size distribution may include a range of about 100 nm to about 600 nm where the treatment site includes an alveolus, a lung parenchyma, or a capillary bed.

The plant stem cell may include one or more of a plant stem cell extract, a lyophilized plant stem cell, a plant stem cell culture medium, or an intact plant stem cell. The plant stem cell may also include a pharmacologically suitable excipient.

The treated lung, oral cavity or nasopharyngeal condition may include one or more of a cancer, an erosive lesion, asthma, an inflammation, a ruptured blood vessel, an infection, a wound, a burn, and an irritation. The method may treat the condition through one or more of a bronchodilatory effect, a tissue regeneration effect, a tumor suppression effect, a cancer cytotoxic effect, a clearing of free radicals, an anti-inflammatory effect, and a mucus reduction.

DETAILED DESCRIPTION

Figure 1:
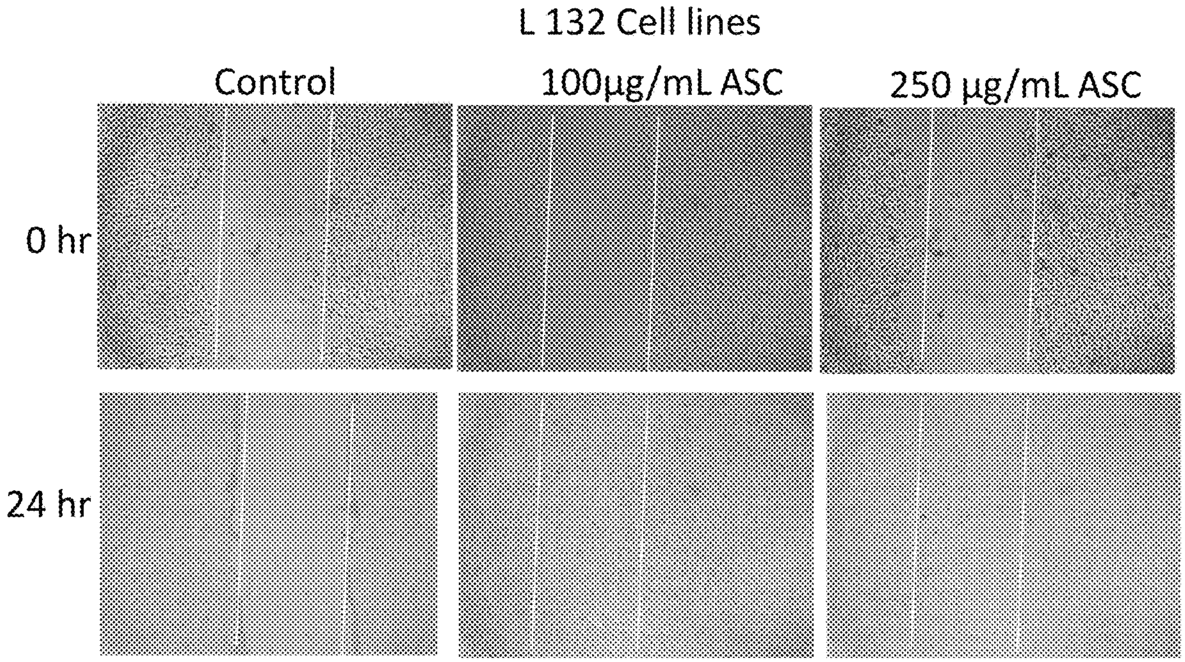
FIG. 1 shows micrographs of selected results of scratch assays in lung epithelial cell cultures treated with an apple stem cell embodiment of the plant extracts of the invention.

I have discovered that plant stem cells beneficially affect human (or other mammalian) tissues and cells. Exposure may be to plant stem cells or to their products, contents, or enriched media (collectively "plant SC products"). As used herein, enriched media refers to culture materials in which plant stem cells are grown and that is subsequently harvested. Such enriched media contains stem cell products, contents, and by-products of plant stem cell growth. The phrase plant stem cell products (alternatively plant SC products) as used herein includes extracts of such cells including products of stem cell lysis or partial digestion, a plant stem cell enriched medium, or an intact plant stem cell.

Human tissues are subject to injury from defects, diseases, insults, injury, trauma, or conditions including one or more of oxidative damage, inflammation, wound healing, or cancer.

Oxidative damage can arise from normal metabolism, including aerobic respiration such as mitochondrial electron transport. Oxidative damage may also arise in response to infectious organisms or immune system action. Oxidative damage may also arise from therapeutic interventions, including radiation therapy. While cells and tissues possess endogenous protective agents against oxidative damage, these agents may be depleted. In some circumstances the endogenous protective agents, which include reservoirs of small molecule antioxidants as well as inducible antioxidant enzymes, may not be adequate to completely prevent oxidative injury. Notably, these endogenous protective agents diminish with age. I have found in a model system that plant SC products have antioxidant activities that may prevent or reduce oxidative damage to affected cells when applied to the cells.

Inflammation is a response of the body to infection, irritation, or tissue damage. Inflammation marshals the body's defenses to effectively respond to these conditions. In some circumstances, secondary effects of inflammation produce additional harm. In other circumstances, inflammatory reactions may arise in inappropriate situations, such as in autoimmune diseases.

Inflammation is mediated by cellular communication, which may be through cell-to-cell contact or through the release of soluble cytokines. These cytokines contribute to modulation of the response, to recruitment of additional cells to the inflammatory process, and to targeted attack against organisms or tissues recognized as foreign. Many cytokines are intimately associated with some of the undesirable effects of inflammation. For example, Tumor necrosis factor alpha (TNF-α) is a cell signaling protein (cytokine) involved in systemic inflammation and is one of the cytokines that make up the acute phase reaction. Specifically targeted injectables, such as humanized monoclonal antibodies with specificity to TNF-α (e.g. adalimumab), can ameliorate some of the undesirable effects of inflammation in autoimmune conditions.

I have found that plant SC products can act upon activated inflammatory cells in a model system to reduce the release of inflammatory cytokines, including TNF-α. The plant SC products may thus have a beneficial effect on inappropriate inflammatory activity when applied to the activated cells. The plant SC products, because they prevent release of cytokines, may have a synergistic effect to agents such as adalimumab because of the different mechanisms of action, e.g. preventing TNF-α release as opposed to inactivating already-released TNF-α.

Wound healing is a beneficial response to insult or injury where cells adjacent to the site of an injury or recruited to the site of an injury respond by closing wounds and repairing or replacing damaged tissue.

I have found that plant SC products can encourage tissue regeneration and wound healing in a model system. The plant SC products may have a beneficial effect on the regeneration of tissues following trauma or injury when applied to the injured tissue. Such injuries are fairly common in the oral cavity because hard foods, such as bone or shell fragments, may be sharp and penetrate portions of the mucosa during chewing. Such injuries are usually minor and heal on their own, but this is not true in all cases and particularly when oral health is compromised by other conditions such as diabetes or immune suppression. Such injuries are less common but not unknown in the nasopharynx. In particular, young children may insert foreign objects through the nose, potentially causing injury. Nose piercing can damage tissue or provide an unprotected access route for microbes. Breathing very dry or cold air may injure nasal mucosa and cause tissue damage or nosebleeds.

Cancer is an abnormal replication and infiltration of cells that have escaped regulatory control. It may be caused by accumulation of mutations at many loci to produce a large variety of phenotypes. Recently developed drugs targeted to specific pathways have been effective against many forms of cancer, but the continuing accumulation of mutations frequently allows some tumor cells to escape this specific therapy.

The fallback treatment in many cases remains cytotoxic agents that kill tumor cells less discriminately. Such cytotoxic agents are valuable if they are more lethal to cancer cells than to the exposed normal cells. A therapeutic ratio of greater than one indicates that a treatment kills cancer cells more readily than noncancer cells. I have found that plant SC products, when applied to cells of a model system, can be more than ten times more effective at killing cancer cells than normal cells. The plant SC products may have a beneficial effect if brought into contact with cancer cells.

Somewhat paradoxically, plant SC products may protect cells from oxidative damage, promote regeneration, and may have a cytotoxic effect. The net effects may depend on access to the treated cells, the inflammatory and oxidative environments, the treatment concentrations and exposure times, or other factors.

Oral cavity and nasopharyngeal conditions may benefit from direct application of plant SC products to oral and nasal tissues. I have invented a suitable method for providing exposure to plant SC to a treatment site in a mammal, including to the respiratory system, the oral cavity, or the nasopharynx. Embodiments of this method use different applicators including aerosol delivery, direct localized contact using adherent applicators, crevice access using flossers, dental surface access using treated brushes or pastes, applicator trays with viscous fillers, gums, chews, lozenges, dissolving oral strips, nasal or oral rinses, nasal packing, and nasal inserts such as dilators, filters, and vents.

Plant stem cells, such as apple stem cells, may stimulate human stem cells, protect against reactive oxygen species or uv-induced cell death, mitigate aging related alterations in gene expressions, and reverse or block telomere shortening. Other plant stem cells such as those from lithy tree, mulberry, *cannabis*, hemp, *chrysanthemum, ginseng*, garlic, mint, grape, *eucalyptus*, lingonberry, lungwort, oregano, plantain, poppy, elecampane, *lobelia*, chaparral (*larrea tridentate*), orchid, osha root, turmeric, ginger, sage, mullein, licorice root, coltsfoot, thyme, *adhatoda vasica, albizzia lebbeck, boswellia serrata, Curcuma longa, ocimum sanctum*, or *piper longum* may have similar or other beneficial effects. In some embodiments, plant SC products may be produced from plant stem cells of vascular plants, such as conifers, ferns, or flowering plants.

In other embodiments, the plant SC products may be produced from plant stem cells of plants with a history of safe human consumption. Especially suitable may be food related species including fruit-bearing angiosperms such as apple, grape, lingonberry, mulberry, plantain, peppers, and other fruit species. Other suitable species include those of seasoning herbs or spices such as turmeric, poppy, ginger, garlic, thyme, oregano, mint, licorice root, sage, and other herb and spice species. These "known safe" plant species advantageously reduce the likelihood of high toxicity as highly toxic species have long ago been removed from the human larder.

In other embodiments, the plant SC products may be produced from plant stem cells of species that have long formed a part of the human pharmacopeia, including *adhatoda vasica*, poppy, rose, hibiscus, *cannabis*, coltsfoot, elecampane, *eucalyptus, boswellia serrata* (frankincense), *ginseng*, hemp, *lebbeck*, lithy tree, licorice root, mullein, and other medicinal species. Since these medicinal species have pharmaceutical actions, they may require further safety testing than the food related species. However, extracts of these species are known to be safe in controlled dosages.

Embodiments of the invention may expressly include any subsets or combinations of the above described species, cultivars, or taxa, optionally excluding any species either listed, unlisted, or within the taxonomic groups listed.

Without intent to be bound by theory, Applicants believe that certain plant stem cells, because they share at least some signal motifs with other eukaryotes including humans, can produce beneficial modulation of human signaling pathways. For example, *Arabidopsis*-type 7-mer stem cell telomerase may act on the repetitive human 6-mer telomere sequence TTAGGG. Asparagales type 6-mer stem cell telomerase may also act on the human telomere with its identical sequence specificity. The long evolutionary distance between human and plant telomerase enzymes suggests that the plant enzymes may act in different circumstances and under different conditions than the human enzyme. This likely different action may fortuitously remedy defects in human metabolism and cell proliferation, particularly when defects are related to cell proliferation or cellular senescence.

There may be other as yet unidentified convergences in plant and human signaling pathways that present further opportunities for therapeutic effects.

Further, since plant stem cells include genes and pathways that may produce biologically active compounds, these cells may be capable of delivering such active compounds to treat human disease.

Plant SC products may be treated by encapsulation to help enhance stability by protecting the plant SC products from exposure to environmental materials or conditions that may degrade the activity of the active materials. Encapsulation may also serve to control the release of active materials to a desired time (e.g. when exposed to an oral cavity surface) or at a desired rate. Encapsulation may be performed by any method known in the art, including those reviewed by Yadav et al. in Peptides 32 pp. 173-187 (2011). This review is hereby incorporated by reference for its disclosure of methods of encapsulation. Any of these encapsulation methods may be used with any of the delivery devices for any appropriate treatment site. Capsules may be ruptured by mechanical action or may leach the active materials on exposure to an aqueous environment.

In some embodiments, a suitable method of encapsulation includes emulsification polymerization using aqueous phase methacrylate monomer and a photoinitator such as benzoin ethyl ether emulsified with plant SC products with polyethylene oxide as a stabilizer and exposure to UV light after emulsification to produce poly(methacrylate) encapsulated active components of plant SC products. The capsules may range from about 50 to about 5000 nm in diameter. While the capsules may be close to monodisperse (depending on the method of preparation), in some embodiments, the size of capsules may be deliberately widely distributed to control the rate of release of active materials. Widely distributed populations of capsules may be prepared by altering the conditions of emulsification during encapsulation or by mixing two or more batches of capsules with different size.

In other embodiments, plant SC products may be encapsulated in liposomes. Liposomes are spherical vesicles bounded by one or more lipid bilayers. The internal environment of a liposome is aqueous; the hydrophobic membrane, formed by the lipid bilayer, retards transit of hydrophilic solutes. The bilayer itself may also accept loading with hydrophobic components of plant SC products, thus providing a vesicle that can transport both aqueous and organic solutes.

Liposomes may be produced by dispersing hydrophobic wall materials in an aqueous solution containing the plant SC products. The materials may be dispersed by a variety of methods such as sonication, extrusion through polycarbonate filters, or hydration of liposome wall components in an aqueous medium followed by heating. The lipid bilayer wall may include a mixture of lipids, cholesteric materials, glycerol, and structural agents such as proteins, polymers, or gums.

In an embodiment, plant SC materials may be encapsulated in liposomes by preparing a lysate of cultured cells in liposomes composed of soy phospholipids (0.14% weight/volume ("w/v")), glycerin (0.4% w/v), and xanthan gum (1% w/v). The liposomes may be suspended in about a 10% suspension in deionized water adjusted to pH 7.4 with 1.4% w/v phenoxyethanol as a preservative. Details of liposomal production are well known in the art: see M R Mozafari, Liposomes: An Overview of Manufacturing Techniques Cellular & Molecular Biology Letters Volume 10, (2005): 711-719, hereby incorporated by reference for its teaching of liposome production methods.

In another embodiment, plant SC materials may be encapsulated in liposomes by hydrating dipalmitoylphosphatidylcholine, dicetylphosphate, and cholesterol, in a 7:2:1 molar ratio in a lysate of plant SC products for 1.5 hours, followed by addition of glycerol (3% v/v). The solution may be mixed at 70-120 Celsius and optionally extruded through polycarbonate filters with pore size of 30-100 nm. The use of dipalmitoylphosphatidylcholine and cholesterol, natural constituents of human tissue, may serve to more readily transfer lysosome content to tissues of the oral mucosa or other portions of the oral cavity.

In other embodiments, plant SC products may be encapsulated in a polylactide co-glycolide polymer matrix. Polylactide co-glycolide is a biodegradable polymer with a history of safe human use. It breaks down upon exposure to water to lactic acid and glycolic acid. Small amounts of these breakdown products are readily metabolized, though larger amounts of glycolic acid can produce renal toxicity. Such capsules can release their contents when exposed to a wet treatment site. Water slowly breaks down the polymer releasing the plant SC product content. This produces a sustained supply for extended treatment.

Polylactide co-glycolide capsules in the low μm size range may be prepared by an emulsion-evaporation procedure that requires mixing of the plant SC products with an organic solvent such as methylene chloride. Water is withdrawn from the ripening capsules in an evaporation step. See Sah E and Sah H, *Journal of Nanomaterials*, vol. 2015, Article ID 794601, 22 pages, 2015 https://doi.org/10.1155/2015/794601, hereby incorporated by reference for its teaching of polylactide co-glycolide encapsulation.

When intact plant stem cells are used, any capsules must be as large or larger than the size of the cells. When plant stem cell contents are extracted or removed from the intact cells then the capsule size is no longer limited by the cellular size. Such capsules may be selected primarily based upon the targeted region of the lung or upon sizes that may be more compatible with aerosolization processes. For example, if plant stem cell contents are removed by lysis, homogenization, or ultrasonic disruption, or when plant SC products include an enriched medium that is subsequently harvested (and optionally further purified or concentrated), these removed contents may be encapsulated.

In other embodiments, encapsulated plant SC products may be prepared as phospholipid nano-emulsions or as nano-liposomes.

In other embodiments, encapsulated plant SC products may be prepared using the apparatus and method described in US patent publication 2008/0182019 entitled Hollow Microsphere Particle Generator. This publication is hereby incorporated by reference for its disclosure of methods of encapsulation of aqueous phase materials.

Capsules containing plant SC products may be washed by dialysis, by centrifugal filtration, by tangential flow filtration, by centrifugation and decanting, or by other techniques known in the art, to produce washed encapsulated plant SC products. Washing helps remove unreacted monomers or initiator as well as materials not incorporated in capsules. Alternatively, and depending on the materials used in the encapsulation process, encapsulated plant SC products may be used without further processing. After washing, encapsulated plant SC products may be resuspended in a buffer, in sterile saline, in water, or in a suspension containing other excipient materials such as humectants, viscosity modifiers, abrasives, or organic solvents.

In some embodiments, the resuspension material may have viscosity, heat capacity, or hydrophilicity selected to optimize aerosolization of the plant SC products. In other embodiments, the capsules may be dried and mixed with other materials such as polymers for casting adherent dressings. In still other embodiments, the capsules may be mechanically entrapped in applicator devices such as dental flossers or brushes. Capsules containing plant SC products may also be further mixed with high viscosity materials to form pastes together with mild abrasives such as titanium dioxide or baking soda As discussed above with respect to Ephedra, systemic application of plant products may cause unwanted effects. Further, some plant cell compounds may not be well absorbed systemically as discussed above for unconjugated quercetin. Most macromolecules cannot be administered through the digestive system because proteins are digested before they are absorbed into the bloodstream. Also, their large size prevents them from naturally passing through the skin or nasal membrane, and therefore they may not be administered transdermally without the use of penetration enhancers.

There remain a range of administration methods that can bring plant SC products into contact with tissue to be treated. These include ingestion in protected form, injection, transluminal arterial or venous delivery, topical application to mucous membranes of the mouth, nose, eyes, oropharynx, genitals, or digestive tract, or topical application to skin with penetration enhancers. These administrative routes involve specialized delivery devices.

In embodiments, the invention includes a plant SC product and a delivery device configured to deliver the plant SC product to a particular location of the body including tissues in the oral cavity or nasopharynx. This beneficially supports localized treatment to avoid untargeted effects. The delivery device may be a mechanical applicator that contacts the plant SC products adjacent a treated area, or it may be a vehicle composition that exposes the plant SC products to a portion or the entirety of the oral cavity. Mechanical applicators may be any of an aerosolizing device, an adherent applicator, a flosser, a treated brush, an applicator tray that fits around some of the teeth. Other mechanical applicators include a nasal insert, nasal packing, an injection device, a topical applicator, an eyedrop applicator, an eardrop applicator, or a catheter. Vehicle compositions include a paste, a gum, a chew, a lozenge, a dissolving oral strip, or an oral rinse. The inventive delivery device also includes devices with a similar ability to deliver an aliquot of plant SC products to a targeted treatment site.

There may be no clear division between a mechanical applicator and a vehicle composition. For example, an aerosolizing device is a mechanical applicator but delivers a mist of plant SC products that may form a vehicle. A brush may deliver a paste vehicle composition. An applicator tray may work in tandem with a viscous vehicle to localize the plant SC products at a desired treatment area. A viscous adherent carrier may be mechanically entrapped in a limited area of the oral cavity, such as a gingival pocket. This application uses the term delivery device to encompass a mechanical applicator, a vehicle composition, or a combination of these.

An injection device may comprise a syringe and hollow needle sized for subcutaneous injection, for intradermal injection, for intramuscular injection, for intravenous injection, for intracapsular injection, intraarticular injection, for intraosseous injection, for intraperitoneal injection, for intracavernous injection, or for cardiac injection. These devices are well-known in the art and will not be further described.

Catheters may be used as delivery devices to deliver plant SC products to the gastrointestinal system or to the urethra or bladder. Angio-catheters may be used as delivery devices to deliver plant SC products to any of a large number of selected locations in the vasculature. For example, a catheter inserted transluminally into the femoral or the brachial artery can reach most major blood vessels to deliver plant SC products to the vasculature of an organ or a localized segment of tissue. These devices are well-known in the art and will not be further described.

Topical applicators exist in a variety of forms such as cotton or foam-tipped swabs, adhesive patches, wound dressings, pipettes, and bandages. When a surface of the oral cavity (or other treatment area) is injured and the treatment is of the injury directly, the topical applicator may be directly applied to the injured surface. However, such direct topical application may be ineffective inside the mouth because medications intended for topical application are quickly rinsed, diluted, or scoured away by normal oral cavity action. The delivery devices of my invention avoid or limit this problem and permit effective oral cavity treatment by the plant SC products of my invention.

When used to apply plant SC products to uninjured skin, a topical applicator may incorporate permeation enhancers. Permeation enhancers may reversibly compromise the skin's barrier function and allow the entry of otherwise poorly penetrating materials. Permeation enhancers include materials such as fatty acids, terpenes, fatty alcohol, pyrrolidone, sulfoxides, laurocapram, surface active agents, amides, amines, lecithin, polyols, quaternary ammonium compounds, silicones, or alkanoates.

In some embodiments, the skin's barrier function may be degraded mechanically by delivery devices that abrade surface skin (dermabrasion) or pricking with sharp applicators such as microneedle arrays. In other embodiments the skin's barrier function may be degraded electrically by applying an electroporation voltage to the treated region.

Plant SC products in the form of eyedrops may be administered to the sclera of the eye using a pipette as the delivery device. Similarly, plant SC products in the form of eardrops may be administered into the ear canal.

An aerosolizing device delivers finely divided droplets. Aerosols containing plant SC products may be produced by a variety of devices including sonic nebulizers, e-cigarettes, vaporizers, powder or liquid droplet inhalers, humidifiers, or nasal sprays. In some embodiments, plant SC products may be delivered to tissues of the oral cavity via an aerosolizing device such as an e-cigarette. While an aerosol from such a device does not persist for long periods of time, an e-cigarette or other personal vaporizer may be drawn from repeatedly with the aerosol held in the mouth of the user for from five to thirty seconds to maximize therapeutic contact. The aerosol may be replenished with subsequent "puffs" of the device extending the effective treatment contact time.

The size of aerosol droplets, their concentration, and airflow velocity profile determine the distribution of inhaled product delivery.

In some embodiments, the plant SC products include an excipient. Suitable excipients include one or more of lactose, mannose, sodium chloride, poly lactic acid, poly (lactic-co-glycolic acid), glycerol, glycol, a surfactant, or a liposome. The excipient may serve to buffer the plant SC products or to adjust its viscosity or heat capacity to tune the aerosol generation process. Excipients may also adjust hydrophilicity of the materials to control aerosol particle size.

The location of deposition of aerosolized particles depends on aerosol size distribution, sometimes expressed as mass median aerodynamic diameter (MMAD). Fine aerosols are distributed in peripheral airways but deposit less material per unit surface area than larger particle aerosols because their volume is lower. Larger particle aerosols deposit more drug per unit surface area, but this is preferentially targeted to larger airways. The precise location of deposition depends on airway caliber and structure, which differ between individuals. In general, large conducting airways and oropharyngeal region receive aerosols with a MMAD of 5-10 μm. Smaller particles (1-5 μm in diameter) deposit in small airways and alveoli. More than half of 3 μm particles deposit in the alveolar region. Thus, by selecting an aerosol particle diameter in the range of 5-10 μm or above, aerosolized plant SC products may be at least partially confined to the oral cavity or nasopharynx. This minimizes unintended treatment of the lungs and peripheral airways.

Individual pathology differences can also affect aerosol deposition. For example, the airway narrowing in mild to moderate asthma is more responsive to 2.8 μm aerosols than to either 1.5 μm or 5 μm aerosols. This is likely due to a combination of penetration depth and distribution of affected tissue since smooth muscle (the tissue that produces airway narrowing) is not present in the alveolar region.

The size of particles in the respiratory system is not necessarily the same as when introduced because of the high relative humidity. A hygroscopic aerosol delivered at relatively low temperature and humidity into one of high humidity and temperature would increase in size during inhalation. This effect is more important for smaller particles because of their higher surface area relative to volume. Suitable excipients such as salts or sugars may control water absorption for a more predictable aerosol size distribution.

Particles not deposited during inhalation are exhaled and thus lost. Deposition due to sedimentation affects particles down to 0.5 μm in diameter, whereas below 0.5 μm, the main mechanism for deposition is by diffusion.

The distribution of deposition of aerosolized particles also depends on the position of the patient. For example, in experiments with 4 micrometer aerosols, N R Labris and M B Dolovich in *Br J Clin Pharmacol,* 56, 588-599 reported a 2:1 ratio between lower and upper lobes when the treated person was upright. This gradient is reduced when the patient is supine.

Inhalable aerosols may be produced in a variety of methods including swirl nozzles, venturi atomizers, T-jets, vibrating-mesh nebulizers, heated wicks, vibrating nozzles, and electrospray systems, among others. Most involve the interaction of a gas stream (usually air) and a liquid flow to break up the liquid into discrete particles separated by the flowing air. Suitable methods for delivering the plant SC products may be categorized by the source of the gas stream and by how the liquid flow is broken up.

For inhaled aerosols, the gas stream may be produced by a pump or stored gas or by breathing. Pump or stored gas-based methods advantageously offer repeatable flow rates and pressures and can reduce the work a user need perform to inhale an aerosol. This reduction of work may be of consequence when the treated patient has reduced lung function.

In some embodiments, the invention delivers the plant SC products using a nebulizer or a pressurized metered-dose inhaler. Nebulizers and pressurized metered-dose inhalers use pumps and stored gas to advantageously produce aerosols that may be less dependent on user technique.

Nebulizers are common medical devices that use air pumps to produce (or help propel) aerosols for therapy. These convert liquids or suspensions into aerosols with a particle size that can be inhaled. There are pneumatic jet nebulizers, ultrasonic nebulizers, and mesh nebulizers. Some nebulizer designs may be breath-enhanced or breath-actuated. These devices are well-known in the art and will not be further described.

Medical nebulizers advantageously permit adjustment of flow rates and (indirectly) aerosol size distribution. This permits more accurate targeting of delivery of plant SC products to the desired treatment location.

The pressurized metered-dose inhaler is a commonly-used device that uses stored gas under pressure for aerosol production and delivery. There are press-and-breathe and breath-actuated pressurized inhaler designs. These devices are well-known in the art and will not be further described.

Pressurized metered-dose inhalers advantageously are portable and easily operated. These devices typically are designed for use with relatively high concentration medications (such as albuterol for asthma) so that aerosol volume per actuation is usually small. In some embodiments, the invention includes use of pressurized metered-dose inhaler loaded with plant SC products and an inert drive gas. In such embodiments, the plant SC products may be concentrated to provide an effective dose in one or a few operations.

In other embodiments, the invention delivers plant SC products using a device where the gas stream is produced by breathing. Such systems advantageously allow for aerosol delivery over an extended period of time without interfering significantly with other life activities. This may especially valuable when treatment aerosols comprise fairly low concentration materials. Many plant SC product treatment compositions may be of fairly low concentration.

Breathing-based aerosol delivery devices include personal vaporizers, also known as electronic cigarettes or e-cigarettes. Most personal vaporizers use heat to produce an inhalable aerosol from a liquid or suspension drawn into a wick by capillary action. Users inhale these aerosols and can control puff pressure, puff length, and interval between puffs. With some devices, current applied to the heater may be adjusted.

Typical aerosols from personal vaporizers have particle diameters in the 250-450 nm range and particle density concentration of approximately $10^9$ particles/$cm^3$. These relatively small aerosol particles target a user's entire respiratory system, including the lung alveolar region. Such aerosol size distributions may be useful where there is a benefit from treating the lung as well as the oral cavity or nasopharynx. Because they may be used for extended period, a user may alter posture between upright and supine to better distribute the aerosols to a targeted region.

In other designs, piezo-electric, ferroelectric, or magnetostrictive vibrators may produce the aerosol. Use of personal vaporizers including vibration to produce aerosols may advantageously produce an unheated aerosol that may be adjusted for particles in the micrometer range. This may be particularly appropriate for plant SC products that more exclusively target the oral cavity and especially those that include intact cells.

Although the variations in user operation parameters such as puff pressure can affect the rate of plant SC product delivery, use of personal vaporizers can compensate for these variations by loading a predispensed dose of plant SC product into the personal vaporizer. The device may then be used until the preloaded dose is exhausted. This may be especially advantageous where extended treatment times are desired, as may be the case with plant SC products applied to the oral cavity since each puff produces only a transitory exposure. Repeated puffs prolong the effective exposure permitting a more thorough treatment.

Personal vaporizers may be designed (or adjusted) to produce a controlled aerosol particle size by adjusting the size of the capillary openings in the heated wick, by adjusting the current to the heater, or by adjusting the viscosity and heat capacity of excipients mixed with the plant SC materials. The inventive method may include such adjustments to control the aerosol size distribution. In embodiments, the size may be adjusted to produce aerosols having a size distribution in the range of about 100 nm to about 600 nm where the treatment site includes an alveolus, a lung parenchyma, or a capillary bed. Where the treatment site includes a bronchus or a bronchiole, the particle size distribution may be adjusted to include particles in a range of about 0.5 to 5 μm. Where the treatment site includes the oral cavity or nasopharynx, the particle size distribution may be adjusted to include particles of about 5 to 10 μm.

Many personal vaporizers include breath sensors that may permit adjustment of heater current during inhalation. In some embodiments, the invention includes tuning of heater current to produce a desired aerosol size distribution. This may include individual adjustment based upon breath sensor measurement.

In other embodiments, plant SC products may be delivered as part of a smoke or vapor. In such embodiments, the plant SC products may be mixed with a smoking material to be smoked, such as tobacco or *cannabis*, or may be applied to a support material such as a smoking paper used for wrapping tobacco or *cannabis*. In other embodiments, where a pipe, "bong," hookah, cigarette holder, or filter is used as part of the smoking method, these accessories may be coated with, dosed with, or exposed to plant SC products. In this document, the term smoking materials includes any and all of these accessories, any smoking herbs such as tobacco or *cannabis*, and any consumables used in smoking, such water, juice, flavoring, or other materials added to a water base of a hookah. In some embodiments, plant SC materials may be added to a liquid in the water base of a hookah. In such embodiments, the plant SC materials interact with smoke after the combustion process. In other embodiments, plant SC products may be combusted together with flammable smoking materials. While some plant SC products may not survive combustion, other may be delivered to the oral cavity, the respiratory tree, or the lungs. These plant SC products may help protect tissues exposed to smoke products from their well-known detrimental effects.

Plant SC products may be applied to a smoking paper from a liquid suspension. The smoking papers may then be dried entrapping the products within the porosities or on the surfaces of the smoking paper. The treated smoking papers may then be used in a conventional manner to wrap tobacco, *cannabis*, or other smoking materials. In use, the burning and inhalation process mobilizes some or all of the plant SC products and delivers them to the oral cavity and respiratory system of the user. In some embodiments, the plant SC products may be encapsulated.

In other embodiments, the invention includes plant SC products applied through other delivery devices including adherent dressings, flexible strips, treatment trays, viscous adherent carriers, brushes, flossers, pastes, gums, chews, lozenges, dissolving oral strips, and oral rinses.

Adherent dressings are similar in concept to conventional wound dressings in that a flexible "bandage" is applied to part of the oral cavity. Conventional bandages are generally not effective because the wet environment of the oral cavity impedes adherence.

Adherent dressings may be produced as strips of mucosally adherent materials such as that described in US 2005/0226915 A1 to Haley, incorporated by reference for its disclosure of production of such strips. Strips may be cast of hydrophilic porous polymers having a melting point higher than human mouth temperatures. Suitable materials include carboxymethylcellulose, hydroxymethylcellulose, polyacrylic acid, agar, carrageenan, or gelatin. Gelatin may be particularly useful as its constituent collagen fibers adhere well to collagen fibers in the oral mucosa.

The structural and adherent materials of these flexible dressings may be admixed during production with encapsulated plant SC materials such as the polylactide co-glycolide capsules or liposomes disclosed above. Other similar dressings known in the art may also be combined with plant SC products. The plant SC products may alternatively be packaged as capsules mechanically applied or entrapped to the surface of the dressings.

The adherent dressings are substantially planar flexible patches that conform to and stick to the surface of oral mucosa. The dressings may be affixed to an area of oral mucosa to treat affected areas of tissue. Flexibility of the materials allow continued adherence even as the treated area moves and deforms. Such strips advantageously deliver plant SC products and allow for sustained release of the medication while isolating the treatment area from the remained of the oral cavity. The dressings resist unintended removal by normal oral action but eventually erode. The dressings may be replaced at intervals to continue treatment. In some embodiments, the adherent materials may be cast onto a backing to provide further structural support. Backings may include porous materials such as paper. The porosity helps to mechanically entrap the adherent materials to the backing. The thickness of the dressings may be in the range of 0.01 to about 2 mm to provide the appropriate degree of flexibility and strength. Dressings about 0.5 to 1 mm in thickness provide a reasonable combination of flexibility, strength, and dressing lifetime.

Flexible strips that adhere to the teeth may be used to treat conditions of the teeth or closely surrounding tissues such as the margin of the gums or any pockets or gaps formed between the teeth and gum line, when gum recession occurs. Such pockets or gaps create local environments suitable for microbial build up. If left untreated, the supporting tissue and bone structures of the teeth can be damaged with possible tooth loss.

Tooth-adherent flexible strips are roughly planar devices formed as elongated strips that may include flexible polymers. These may include a backing layer and an adhesive layer bound together to produce the completed device. The adhesive layer may be admixed during production with encapsulated plant SC materials such as the polylactide co-glycolide capsules or liposomes disclosed above. The thickness of such strips may be in the range of 0.01 to about 1 mm to provide the appropriate degree of flexibility and strength.

The backing layer provides mechanical strength and prevents inadvertent bonding to non-target tissues. The backing layer may also provide an easily manipulated portion to assist in mounting the flexible strip in the desired treatment position. Backing layers may be non-adherent polymers (e.g. silicone or vinyl) or cellulose-based materials such as coated paper. In some embodiments, the backing layer may have extent greater than the adhesive layer to provide a tab for easy placement.

An adhesive layer may include a mixture of one or more polymers configured for hydration when exposed to water or saliva. The fully hydrated polymer may be from about 30% to about 90% water. In some embodiments, the polymers may be a mixture of polyethylene oxide and polyvinyl alcohol. The polyethylene oxide may have an average molecular weight of about 300,000 to about 900,000 daltons.

In some embodiments, the adhesive layer may adhere to the backing layer and may be mechanically locked thereto when the backing layer is at least partially porous.

Additional information about the composition of tooth-adherent strips may be found in US20050100515A1 to Sagel et al., hereby incorporated by reference for its disclosure of such strips.

Treatment trays are mechanical devices that serve to partially isolate a portion of the teeth and adjoining gingival tissue from the larger environment of the oral cavity. Treatment trays are roughly shaped to fit some or all of the teeth. A full tooth tray is roughly U-shaped to match the layout of teeth in upper or lower jaw. The tray has a hollow configured to accommodate the teeth with some adjoining space. This hollow may have a generally U-shaped cross section to enclose a group of teeth. Treatment trays may be formed of any fluid-impervious material that can survive the mouth environment. Polymers are generally preferred because of their formability, light weight, and stability in the wet environment.

Individually fitted treatment trays can be produced using a three-dimensional model of the patients mouth (as determined, for example, by a CT scan) or by preparing an impression to make a mold. In some embodiments, a three-dimensional model of a portion of the teeth may be modified to provide a defined clearance surrounding a treatment volume. The individually fitted treatment tray may then be produced (by stereolithography or other additive manufacturing process) from the modified model.

In some embodiments, treatment trays may be fitted with compliant liners that contact the treatment areas when the tray is positioned. These liners may be preloaded with plant SC products so that the treatment area may be exposed for as long as the treatment tray is in position. In other embodiments, the treatment tray may be preloaded with a viscous gel or paste vehicles containing plant SC products. Such gels or pastes require viscosity and surface tension sufficient to hold the plant SC treatment materials in contact with the treatment area while the tray is in position. Suitable materials to provide the required viscosity are gelatin, food gums, or hydroxy methylcellulose, among others.

Large-size treatment trays, such as those used to prepare dental impressions, may be too uncomfortable to hold in the mouth for more than a few minutes. However, when trays more closely approximate the teeth, they may be comfortably held in the mouth for longer periods. Individually fitted tray may be very compact since they conform to the teeth of the patient. Such individually fitted trays are worn with relative comfort for many hours at a time for teeth alignment use and hence may be particularly suitable when extended treatments are required.

With a treatment tray in place, the treated teeth are protected from some influences normally present in the oral cavity. Mechanical action is impeded by the tray; treatment materials in a treatment tray are protected from chewing, swallowing, and worrying action of the tongue. The high viscosity of the treatment composition retards loss of plant SC materials by diffusion into saliva.

Viscous carriers resemble the gels or pastes used with the above described treatment trays. These viscous carriers include viscosity modifiers to provide a viscosity sufficient to hold an aliquot of the viscous carrier in position in a protected area of the oral cavity. These may be applied to relatively protected areas of the oral cavity to provide plant SC product treatment to those areas. Suitable areas for application of these materials include locations where they may be mechanically trapped. For example, a viscous carrier including encapsulated plant SC products in a gelatin, alginate, food gums, hydroxy methylcellulose, or similar viscous material may be inserted mechanically into a dental cavity of the teeth, into pockets between teeth and gums in gum recession, between closely spaced teeth, or into the socket of pulled tooth. Mechanical insertion may be by means of a syringe, a spatula, a probe, a pipette, or by another similar accessory.

Viscous carriers containing plant SC products provide these products to a treated area until they are dislodged, dissolved, exhausted, or removed. The rate of at least some of these processes may be controlled by selection of the viscous carrier materials. A viscous material with a relatively high melting point and low solubility may survive in place for hours to days. However, high melting points may be problematic because of possible burns during insertion. Alginate materials resist water solubilization when combined with calcium ions. Viscous materials incorporating calcium alginate provide a long lifetime without high temperature during application. In some embodiments, the invention includes plant SC products applied in such a paste. The plant SC products may be encapsulated or unencapsulated; encapsulated product may have better stability, but unencapsulated product allows more free diffusion in the viscous carrier medium.

Brushes such as conventional toothbrushes can apply plant SC treatment materials to the teeth and surrounding tissue. Such treatment is transitory, but this may be adequate for some applications. Brushes can include plant SC products within the brush bristles. This is particularly efficacious when the plant SC products are encapsulated and adhered to the bristles. Mechanical action of brushing may serve to rupture the capsules, delivering the plant SC materials to the treatment areas. The plant SC products may be mechanically entrapped in bristle fibers or may adhere to bristles through adhesives such as methyl 2-cyanoacrylate, which may be applied to brush bristle material or to the bristles of completed brushes. The bristles may then receive dried encapsulated plant SC products. This technique may be particularly appropriate when the plant SC products are encapsulated in poly(methacrylate) as described above.

In other embodiments, bristles may be treated with a relatively sticky binder admixed with the dried plant SC product capsules. The binder may be a polyethylene glycol wax, a microcrystalline wax, a liquid polyethylene glycol ester of beeswax, or other waxes, polymers, or gums that have a sticky texture. The resulting bristles may be rubbed against the teeth or other relatively hard structures of the oral cavity to transfer at least some of the capsules and associated binder to the surface of the teeth or other structures. Thus, though brushing applies plant SC products for a relatively short time, a portion of the plant SC products may adhere to the tissue to be treated providing a longer duration of treatment.

Plant SC products may also be applied to the oral cavity as pastes in a similar manner to conventional toothpaste. Plant SC products either encapsulated or unencapsulated may be admixed with a paste base that includes ingredients for cleaning the teeth or other surfaces. In some embodiments, the paste base may contain mild abrasives such as sodium bicarbonate particles of less than about 20 μm in average size, a humectant and a thickener. The paste base may also include a surfactant. The abrasive may constitute between about 30% and about 70% by weight of the paste. Humectants may include a propylene glycol, a glycerol, a polyethylene glycol, a sorbitol, or similar hydrophilic materials about 8 to 35%, by weight. Useful thickeners include methyl cellulose, sodium carboxymethylcellulose, hydroxyethyl cellulose, carrageen, and food gums such as gum Arabic or xanthan gum. The paste surfactant may include sodium lauryl sulfate, sodium lauroyl sarcosinate, or similar materials. The paste base may also include flavoring or sweeteners.

Plant SC materials may be admixed with the paste base in amounts between 1 and 20% by weight. The composition may then be degassed under vacuum to reduce free carbon dioxide that may evolve from the bicarbonate.

Pastes of this sort may be applied with a brush as part of normal toothbrushing. Mechanical action between the brush, abrasives, and oral cavity surfaces releases the plant SC products to treat exposed surfaces. Though brushing applies plant SC products for a relatively short time, a portion of the plant SC products may adhere to the tissue to be treated providing a longer duration of treatment.

In other embodiments, plant SC products may be applied to treatment areas of the oral cavity through specialized flossers. Flossers include flexible strings or tapes that a user moves between the teeth to remove residual food materials and plaque. Flossers may be fabricated of natural or synthetic fibers and may have handles to support the fibers during use. Suitable natural fibers may include linen, cotton, or silk; synthetic fibers may include polyester, fluoropolymers, nylon, acrylic, rayon, acetate polymers, polyethylene, polypropylene, or other materials alone or in combination.

Flossers may include a binder such as a polyethylene glycol wax, a microcrystalline wax or a liquid polyethylene glycol ester of beeswax, or other waxes, polymers, or gums that have a sticky texture. Plant SC products are incorporated into the flossers. In some embodiments, the plant SC products (either encapsulated or unencapsulated) are mixed with a binder before the binder is applied to the flosser fibers. In other embodiments, a flosser including a binder may be treated with plant SC products (especially encapsulated plant SC products) so that the products stick to the binder. In other embodiments, plant SC products may be absorbed into or mechanically trapped by the fibers of flossers.

Mechanical action between the flosser and oral cavity surfaces releases the plant SC products to treat exposed surfaces. In some embodiments, a portion of binder from a flosser and its bound or entrapped plant SC product may be transferred to the dental surface to provide extended treatment to the surrounding area of the oral cavity. This is especially beneficial between teeth where mechanical action is reduced as compared to the oral cavity as a whole. Reduced mechanical action may encourage microbial growth or inflammation. This same reduced action beneficial shields deposited plant SC products for longer treatment periods.

Chewing gums are soft, cohesive substances that are chewed without being swallowed. Chewing gum usually includes a gum base admixed with flavorings or sweeteners. In embodiments, the invention includes a chewing gum admixed with plant SC products. The plant SC products are preferably encapsulated in polymeric capsules or liposomes as described above.

The action of chewing gum mechanically moves the gum into contact with portions of the oral cavity, particularly the teeth and tongue and maintains proximity for extended periods. The mechanical action releases the plant SC products and may also rupture the capsules so that the plant SC products directly contact treated areas.

Chews are non-gum materials that are chewed without being swallowed. Such chews are frequently plant matter such as leaves, stems, or treated nuts. Among such chews are "smokeless" tobacco, coca leaves, *cannabis* preparations, and *betel* nut. Such chews are often associated with deleterious health effects. For example, effects of *betel* nut chewing include cancers of the mouth and esophagus; its use has been linked to oral submucosal fibrosis. chewing tobacco can cause cavities, abrasion of teeth, teeth staining, gum disease, receding gums, bone loss around roots, and tooth loss. In embodiments, the invention includes plant-based chews admixed with plant SC products. The plant SC products are preferably encapsulated in polymeric capsules or liposomes as described above.

The action of mastication mechanically moves the chew into contact with portions of the oral cavity, particularly the teeth and tongue. It maintains that proximity for extended periods. The mechanical action releases the plant SC products and may also rupture the capsules so that the plant SC products directly contact exposed areas. Advantageously, the plant SC products are exposed to the same areas as those potentially damaged by extensive use of the chews themselves. The plant SC products may serve to reduce, prevent, or repair such damage.

Lozenges (also known as throat lozenges or cough drops) are a small, typically medicated tablet intended to be dissolved slowly in the mouth to temporarily stop coughs, lubricate, and soothe irritated tissues of the throat. When mounted to an external holder, lozenges may be known as suckers or lollipops. Lozenges typically contain sugars, gelatin, or pectin to control the rate of dissolution. In embodiments, the invention includes oral treatment lozenges that contain plant SC products. The plant SC products are preferably encapsulated in gelatin capsules or liposomes as described above.

The action of sucking on a lozenge (or of combined sucking, movement about the mouth, and mastication) gradually releases the medicated content over an extended period. The released material comes in contact with surfaces of the oral cavity, providing treatment of those areas.

Dissolving oral strips are approximately postage stamp sized devices that include hydrophilic polymers. These rapidly dissolves on the tongue or buccal cavity, delivering their content to the oral cavity. Commonly, dissolving oral strips are used with breath fresheners, but some systemic medications are available in this form. In embodiments, the invention includes dissolving oral strips that contain plant SC products. The plant SC products are preferably encapsulated in gelatin capsules or liposomes as described above. In use, the dissolving oral strips are introduced into the mouth and placed atop or beneath the tongue or adjacent the buccal mucosa.

Dissolving oral strips film may be formed of gelatin mixed with starches such as tapioca starch, low molecular weight corn starch, or low molecular weight potato starch, or with alginates. The strips may be plasticized by addition of sorbital, other sugar alcohols, glycerol, or propylene glycol. In embodiments, the encapsulated plant SC materials may be added to these ingredients and the combination cast or extruded and then dried. The dissolving oral strips are typically less than 0.050 mm thick.

Exposure of the dissolving oral strips to the moist environment of the oral cavitied releases the content in a relatively brief period of time, but the length of this time may be manipulated by increasing the thickness of the strips (about 0.1 mm to about 0.5 mm thick) or by varying the composition using polymers more resistant to dissolution. The use of strips thicker than about 0.1 mm advantageously increases the exposure time of the plant SC products to the tissues of the oral cavity. The use of dissolving oral strips may be particularly advantageous where the desired treatment site is in a relatively protected area of the oral cavity such as beneath the tongue.

In other embodiments, plant SC products may be applied to a large portion of the oral cavity via an oral rinse. An oral rinse is a treatment composition that a user swishes about the mouth or gargles to apply a treatment for a limited period of time. A nasal rinse is similar but intended for use in the nasopharynx. Generally oral rinses include one or more of antimicrobials, surfactants, perfumes, or fluorides. Conventional oral rinses generally include a large proportion of alcohols such as ethanol; these are generally not included in nasal rinses. Oral rinses are usually intended to be spit out rather than swallowed because they may contain ingredients that can be toxic if ingested in large amounts.

The oral and nasal rinses of the invention may include any of the components of conventional oral rinses. The rinses include plant SC products either encapsulated or unencapsulated. Rinses may contain antimicrobial agents or preservatives, salts adjusted to roughly physiological concentrations (e.g. 9 g NaCl per liter) and preferably are sterile. In some embodiments, the oral rinses include encapsulated plant step cell products intended to stick to surfaces of the oral or nasal cavity and remain in position for an extended treatment period. In one embodiment, the rinse contains poly(methacrylate) encapsulated active components of plant SC products as described above and ethanol. The ethanol induces softening and plasticization of poly(methacrylate) capsules. These softened capsules may stick to surfaces of the oral cavity during application of the rinse and remain in position once the rinse solution is expelled. Similar results may be obtained with other encapsulation methods where the rinse contains an agent that makes the capsules sticky. In other embodiments, the plant SC products may be dissolved or suspended in the rinse without encapsulation.

A nasal rinse may be introduced into the nose using a pipette, medicine dropper, squeeze bottle, neti pot, or other irrigation device.

In some embodiments, capsules are naturally sticky and can adhere to portions of the oral cavity. For example, gelatin-based capsules contain collagen, which can adhere to native collagen of the oral mucosa. Administration of rinses containing gelatin-based capsules allows the capsules to stick and subsequently deliver plant SC products over an extended period.

In some embodiments, the delivery device may include nasal packing. Nasal packing is an absorbent wadding such as gauze or cotton roll used to control bleeding within the nose. Nasal packing may be treated with plant SC products to bring those products into contact or close proximity with treatment areas.

In other embodiments, the delivery device includes nasal inserts such as dilators, filters, and vents configured to be inserted into the nostrils. These generally pass air and may serve to keep the nostrils open. In some embodiments, nasal vents include a semirigid porous foam plug that allows air to pass through while keeping the nostril open. Such foam plugs may be dosed with particulate plant SC materials (or with liquid plant SC materials and then dried) so that, upon breathing, a portion of the plant SC products may be inhaled with each aspiration. The inhaled products may then come into contact with nasal mucosa for treatment.

The examples below describe a collection of experiments designed to demonstrate the effectiveness of plant stem cell products in model systems comprising cultured cell lines including human cell lines and mouse macrophage cell lines. Scratch assays used a normal human epithelial line to ascertain the effect of plant stems on cell regeneration. A cytokine release assay evaluated anti-inflammatory activity using an activated mouse macrophage cell line. Two human lung cancer cell lines (a lung adenocarcinoma and a squamous carcinoma) were compared to a normal lung epithelial cell line to determine treatment efficacy and cancer-specific cytotoxicity.

Apple stem cell extracts were tested in each of the assay types. Other plant stem cells, as well as other plant extracts, were evaluated in scratch assays using the normal human epithelial line and in cytoxicity assays comparing effects on the human lung adenocarcinoma cell line and the normal human epithelial cell line.

Example 1: Plant Stem Cell Extracts

The following plant stem cell extracts were tested for biological effects. Plant stem cells refer to dedifferentiated replicating cells isolated from a part of a plant regenerating from an injury and their progeny. Injury sites may be from any portion of a plant such as callus, leaves, fruit, stems, flowers, roots, meristem, root cap, or seeds. Other plant stem cells may be derived from cells of a developing plant embryo, from a plant callus, or from plant tissue samples (explants) in tissue culture medium in vitro. Plants stem cells may be derived from many different cell types and may be able to differentiate into a whole plant.

Apple stem cell culture extract (ASC) was purchased from Lotioncrafter LLC of Eastsound, Washington. This composition included a lysate of dedifferentiated cells from *Malus domestica* callus. The cells were derived from Swiss apple variety Uttwiler Spatlauber. The extract was prepared by encapsulating a lysate of cultured cells in liposomes composed of soy phospholipids (0.14% weight/volume ("w/v")), glycerin (0.4% w/v), and xanthan gum (1% w/v). The liposomes were suspended in about a 10% suspension in deionized water adjusted to pH 7.4 with 1.4% w/v phenoxyethanol as a preservative.

Lingonberry Stem Cell (LSC) extract was purchased from MakingCosmetics.com Inc. of Snoqaulmie, Washington. This composition included water, glycerin, *Vaccinium Vitis Idaea* fruit extract, xanthun gum, sodium benzoate, gluconolactone, and calcium gluconate. *Vaccinium Vitis Idaea* is a short evergreen shrub in the heath family that bears edible fruit, native to boreal forest and Arctic tundra throughout the Northern Hemisphere from Eurasia to North America.

Orchid Stem Cells (OSC) extract was purchased from MakingCosmetics.com Inc. of Snoqaulmie, Washington. This composition included water, glycerin, Calanthe discolor extract, xanthun gum, sodium benzoate, gluconolactone, calcium gluconate. Calanthe discolor is a species of orchid native to eastern Asia.

Example 2: Plant Extracts

The following plant extracts other than plant stem cell extracts were tested for comparison with plant stem cell extracts.

Apple Fiber Powder (AFP) was purchased from Starwest Botanicals of Sacramento, California. This composition included powder from *Pyrus Malus*. *Pyrus Malus* is a former taxonomic grouping applied to the apples, pears and related plants of the subfamily Maloideae.

Dandelion Root Extract (DRE) was purchased from Starwest Botanicals of Sacramento, California. This composition included *Taraxcum officinale* root extract, water, and alcohol (30%). *Taraxcum officinale* is a flowering herbaceous perennial plant of the family Asteraceae (Compositae). It can be found growing in temperate regions of the world.

Aloe Vera Juice (AVJ) was purchased from Starwest Botanicals of Sacramento, California. This composition included decolorized aloe barbedensis, citric acid and sodium benzoate. aloe barbedensis is a succulent plant species of the genus Aloe. An evergreen perennial, it originates from the Arabian Peninsula but grows wild in tropical climates around the world and is cultivated for agricultural and medicinal uses.

*Ginkgo* Leaf Extract (GLE) extract was purchased from Starwest Botanicals of Sacramento, California. This composition included *Ginkgo biloba* Leaf extract, water and alcohol (30%). *Ginkgo biloba* is a large tree native to China; the tree is widely cultivated.

Example 3: Target Cells

Human lung adenocarcinoma cell line A549, human squamous carcinoma cells line NCI-H520, and "normal" lung epithelial cell line L132 were procured from National Centre for Cell Sciences (NCCS), Pune, India. RAW 264.7 mouse macrophage cell lines were used for inflammation assays.

Example 4: Scratch Gap Regeneration Assay I

Scratch assay determines effects of a treatment on cell migration and proliferation. In a typical scratch assay, a "scratch or wound gap" is created in monolayer cell culture by scratching and creating a gap in the culture. "Healing" of the gap by growth and cell migration towards the center of the gap is monitored and measured. Various factors that alter the migration and growth of the cells to bridge the gap can lead to increased or decreased "healing" rate of the gap. Scratch assay on normal lung cell line L132 was performed to evaluate regenerative potential of the apple stem cell extract.

Method: Human lung epithelial cell line L132 cells were cultured in Dulbecco Modified Eagle Medium with 10% fetal bovine serum (FBS). Cells were seeded ($0.05\times10^6$) into 24-well tissue culture plate. At about 80% confluence, a scratch in a straight line was created across the center of the well with a sterile 1 ml pipette tip. The long axial of the tip was held perpendicular to the bottom of the well to create a uniform scratch. Wells were washed after the scratch and then supplemented with fresh culture media. Test wells were subjected to the media with the test material at one of 100 and 250 μg per mL of media. Media without added test materials served as a control. Cells were then cultured for another 24 hours, washed twice with PBS and then fixed with 3.7% Paraformaldehyde for 30 minutes. Pictures of the monolayer were taken on a microscope and the gaps were quantitatively evaluated using ImageJ software from (http://rsb.info.nih.gov/ij/download.html). All studies were performed in triplicate. Results of triplicate data points appear in the table below. Concentrations of ASC refer to a mass per volume of the lysate.

TABLE 1

Results of ASC scratch assay as analyzed by ImageJ software. Values are determined width of scratched areas.

| ASC Scratch Assay | replicate 1 initial gap width (mm) | replicate 2 initial gap width (mm) | replicate 3 initial gap width (mm) | Average | SD | SE |
|---|---|---|---|---|---|---|
| Control | 27.32 | 28.90 | 25.55 | 27.26 | 1.68 | 0.97 |
| 100 μg/mL | 24.43 | 25.55 | 26.65 | 25.54 | 1.11 | 0.64 |
| 250 μg/mL | 24.42 | 25.55 | 25.55 | 25.17 | 0.65 | 0.38 |
| **ASC Scratch Assay** | **replicate 1** | **replicate 2 final gap width (mm)** | **replicate 3** | **Average** | **SD** | **SE** |
| Control | 21.21 | 20.23 | 20.21 | 20.55 | 0.57 | 0.33 |
| 100 μg/mL | 12.21 | 13.32 | 13.33 | 12.95 | 0.64 | 0.37 |
| 250 μg/mL | 10.21 | 11.12 | 10.90 | 10.74 | 0.47 | 0.27 |

FIG. 1 shows the physical appearance of scratches in selected wells for this ASC scratch assay. The parallel lines disposed roughly vertically in each image are the boundaries of the scratch as determined by the ImageJ software.

| difference in width: 0-24 hours | replicate 1 | replicate 2 | replicate 3 | mean | standard deviation |
|---|---|---|---|---|---|
| Control | 6.11 | 8.67 | 5.34 | 6.71 | 1.42 |
| 100 μg/ml | 12.22 | 12.23 | 13.32 | 12.59 | 0.52 |
| 250 μg/ml | 14.21 | 14.43 | 14.65 | 14.43 | 0.18 |
| Ratio/control | | | | | |
| 100 μg/ml | 2.00 | 1.41 | 2.49 | 1.88 | 0.22 |
| 250 μg/ml | 2.33 | 1.66 | 2.74 | 2.15 | 0.21 |

Table 2 shows results calculated from the data of from Table 1 where each value was calculated as the difference in gap width between time zero and 24 hours, with replicates compared individually to remove gap width influence on results.

| Ratio/control | mean | standard deviation |
|---|---|---|
| 100 μg/ml | 1.88 | 0.22 |
| 250 μg/ml | 2.15 | 0.21 |

Table 3 shows results calculated from the data of from Table 1 where each value was calculated by forming a ratio of the mean difference of Table 2 to the mean difference of the control wells. Standard deviations were calculated by error propagation assuming errors were uncorrelated. These summary results showed a higher degree of scratch closure for the treated wells, with a higher degree of closure at the higher ASC concentration.

Figure 2:
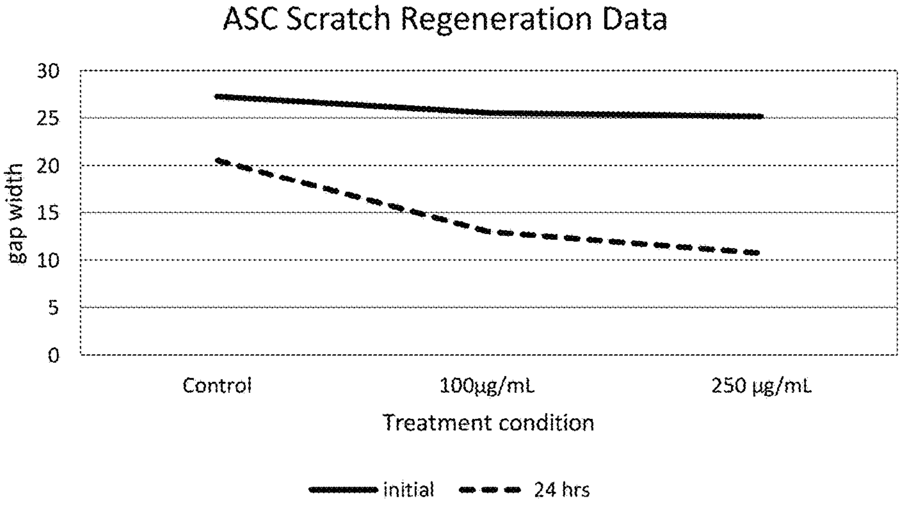
FIG. 2 shows a graph of summary results of the scratch assays of FIG. 1.

FIG. 2 is a graphical representation of these ASC scratch assay results. This shows a clear acceleration in closure of the gap in the treatment group as compared to untreated controls. The apple stem cell extracts produced faster regeneration of the cells in the gap at both the concentrations used after 24 hours treatment. The rate of gap closure was treatment dose dependent. Results were statistically significant at $p\leq0.05$, indicating that apple stem cell extract can exert a positive effect in wound healing and regeneration of lung tissue.

Example 5: Scratch Gap Regeneration Assay II

The experiment of Example 4 was repeated, substituting other plant materials for ASC. Plant stem cell materials included Apple Fiber Powder (AFP), Dandelion Root Extract (DRE), Aloe Vera Juice (AVJ), *Ginkgo* Leaf Extract (GLE), Lingonberry Stem Cells (LSC), Orchid Stem Cells (OSC) as described in Examples 1 and 2. Example 5 experiments were performed with a common set of control wells. Concentrations of each material refer to mass of each as-supplied material. Each material was first prepared as a 1000 μg/mL stock in in Dulbecco Modified Eagle Medium with 10% FBS.

Figure 3A:
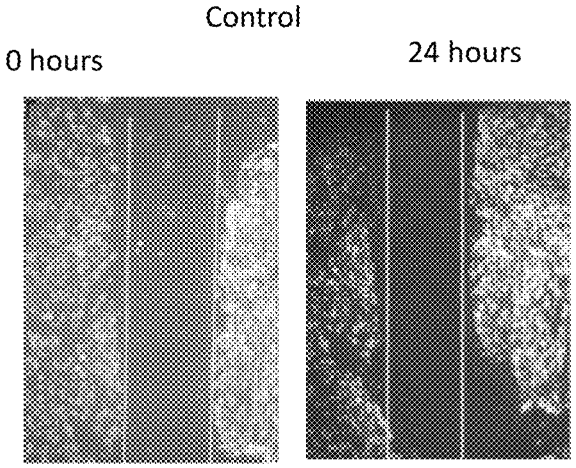
FIG. 3A-3G show micrographs of scratch assays for cells treated with controls or embodiments of plant cell materials of the invention.
Figure 3B:
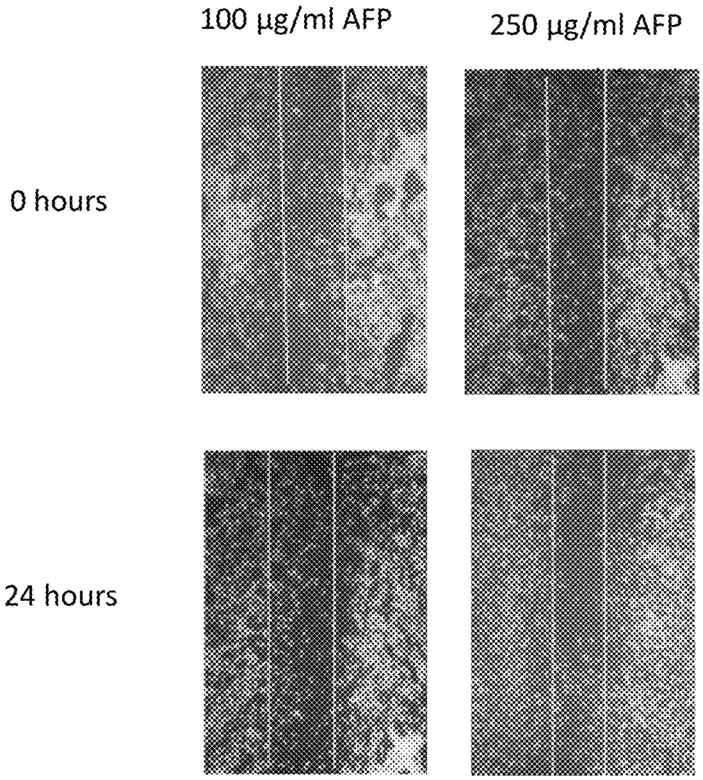
Figure 3C:
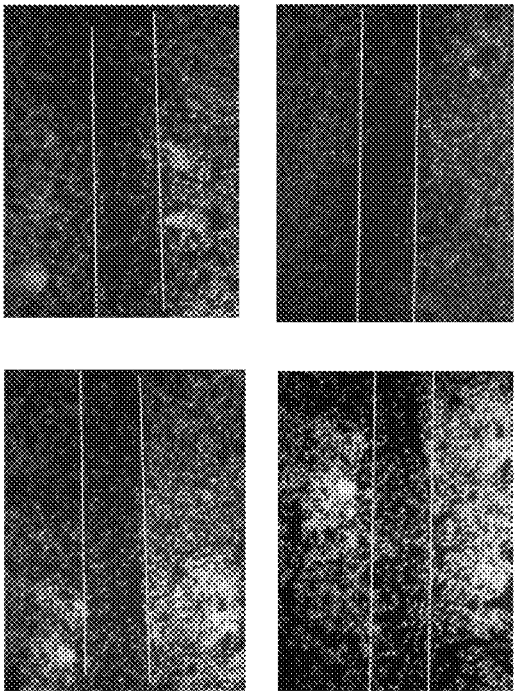
Figure 3D:
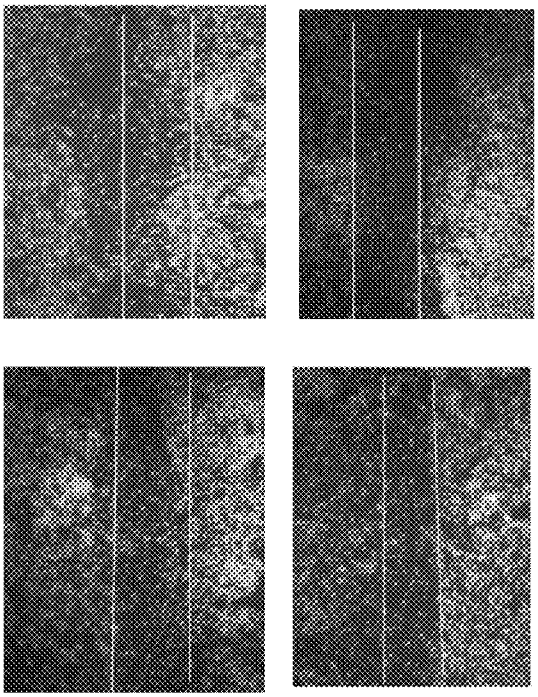
Figure 3E:
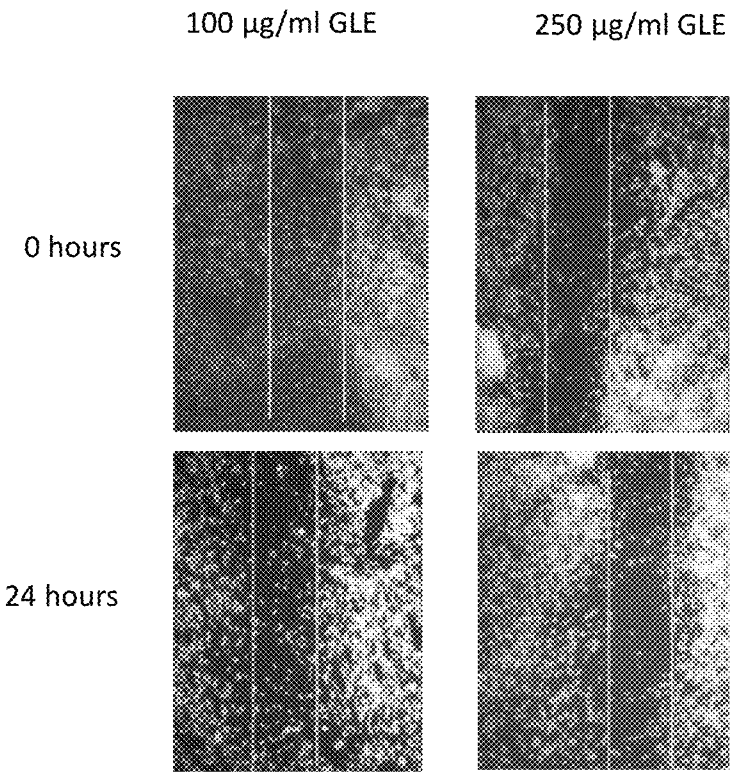
Figure 3F:
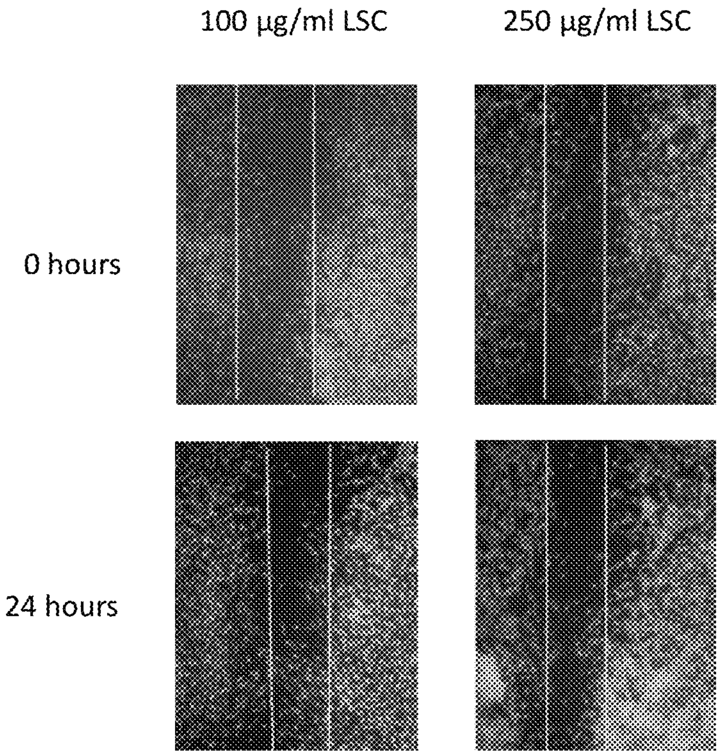
Figure 3G:
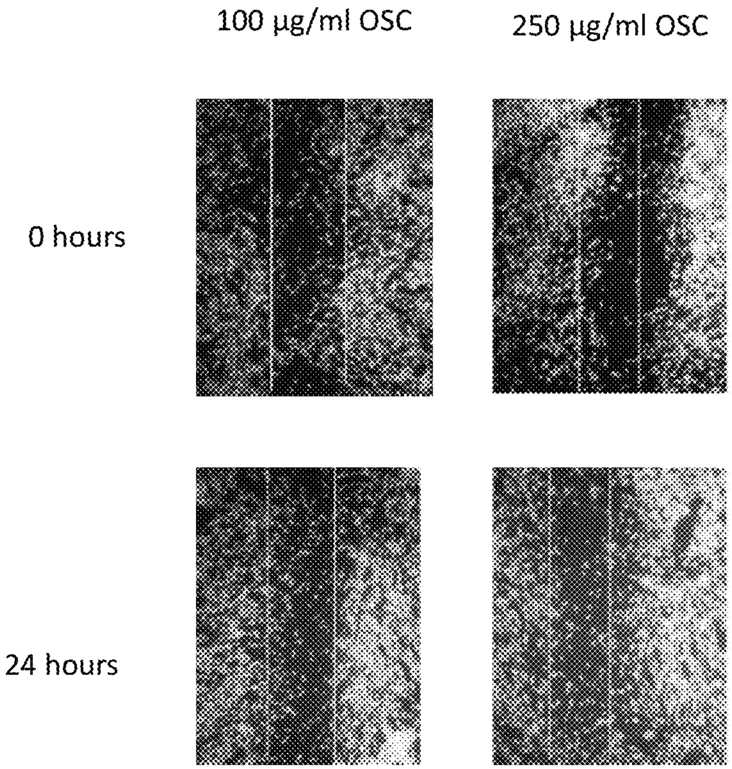

FIGS. 3A-3G shows phase contrast micrographs of selected wells of control and treated cells at the start of the experiment and 24 hours later (fixed with paraformaldehyde). The parallel lines disposed roughly vertically in each image are the boundaries of the scratched region as determined by the ImageJ software. FIG. 3A shows control-treated wells. FIGS. 3B through 3G show one well for each treatment at each concentration at the start of the experiment and the same well 24 hours later. Note the increased number of cells in the scratched gap after 24 hours.

TABLE 4

Results of Control (unaugmented media, AFP, DRE, AVJ, GLE, LSC, and OSC scratch assays as analyzed by ImageJ software. Values are the determined widths in mm of scratched areas at t = 0 and at 24 hours. Entries in rows marked diff. are differences between width of scratched areas at t = 0 and at 24 hours for the same well.

| | replicate 1 | replicate 2 | replicate 3 | Average | SD | SE |
|---|---|---|---|---|---|---|
| Control t = 0 | 28.90 | 29.98 | 29.87 | 29.58 | 0.59 | 0.34 |
| Control t = 24 | 27.89 | 27.75 | 27.65 | 27.76 | 0.12 | 0.07 |
| Control diff. | 1.01 | 2.23 | 2.22 | 1.82 | 0.57 | 0.33 |
| AFP, t = 0 | | | | | | |
| 100 μg/mL | 29.21 | 29.09 | 28.9 | 29.07 | 0.16 | 0.09 |
| 250 μg/mL | 28.9 | 29.78 | 29.88 | 29.52 | 0.54 | 0.31 |
| AFP, t = 24 | | | | | | |
| 100 μg/mL | 26.78 | 25.65 | 25.54 | 25.99 | 0.69 | 0.4 |
| 250 μg/mL | 25.67 | 24.32 | 25.67 | 25.22 | 0.78 | 0.45 |
| AFP diff. | | | | | | |
| 100 μg/mL | 2.43 | 3.44 | 3.36 | 3.08 | 0.46 | 0.26 |
| 250 μg/mL | 3.23 | 5.46 | 4.21 | 4.30 | 0.91 | 0.53 |
| DRE, t = 0 | | | | | | |
| 100 μg/mL | 28.92 | 28.78 | 28.77 | 28.82 | 0.08 | 0.05 |
| 250 μg/mL | 28.9 | 29 | 28.76 | 28.89 | 0.12 | 0.07 |
| DRE, t = 24 | | | | | | |
| 100 μg/mL | 26.21 | 26.55 | 27.21 | 26.66 | 0.51 | 0.29 |
| 250 μg/mL | 26.22 | 25.43 | 25.44 | 25.7 | 0.45 | 0.26 |
| DRE diff. | | | | | | |
| 100 μg/mL | 2.71 | 2.23 | 1.56 | 2.17 | 0.47 | 0.27 |
| 250 μg/mL | 2.68 | 3.57 | 3.32 | 3.19 | 0.37 | 0.22 |
| AVJ, t = 0 | | | | | | |
| 100 μg/mL | 28.97 | 29.29 | 28.78 | 29.18 | 0.53 | 0.31 |
| 250 μg/mL | 28.79 | 28.09 | 28.94 | 28.61 | 0.45 | 0.26 |
| AVJ, t = 24 | | | | | | |
| 100 μg/mL | 25.67 | 26.77 | 26.45 | 26.3 | 0.57 | 0.33 |
| 250 μg/mL | 23.67 | 23.21 | 28.94 | 25.27 | 3.18 | 1.84 |
| AVJ diff. | | | | | | |
| 100 μg/mL | 3.3 | 2.52 | 2.33 | 2.72 | 0.42 | 0.24 |
| 250 μg/mL | 5.12 | 4.88 | 0 | 3.33 | 2.36 | 1.36 |

TABLE 4-continued

Results of Control (unaugmented media, AFP, DRE, AVJ, GLE, LSC, and OSC scratch assays as analyzed by ImageJ software. Values are the determined widths in mm of scratched areas at t = 0 and at 24 hours. Entries in rows marked diff. are differences between width of scratched areas at t = 0 and at 24 hours for the same well.

| | replicate 1 | replicate 2 | replicate 3 | Average | SD | SE |
|---|---|---|---|---|---|---|
| GLE, t = 0 | | | | | | |
| 100 μg/mL | 28.88 | 29.9 | 28.97 | 29.53 | 0.56 | 0.33 |
| 250 μg/mL | 29.09 | 29.78 | 28.9 | 29.26 | 0.46 | 0.27 |
| GLE, t = 24 | | | | | | |
| 100 μg/mL | 27.89 | 26.98 | 26.56 | 27.14 | 0.68 | 0.39 |
| 250 μg/mL | 24.56 | 23.45 | 24.87 | 24.29 | 0.75 | 0.43 |
| GLE diff. | | | | | | |
| 100 μg/mL | 0.99 | 2.92 | 2.41 | 2.11 | 0.82 | 0.47 |
| 250 μg/mL | 4.53 | 6.33 | 4.03 | 4.96 | 0.99 | 0.57 |
| LSC, t = 0 | | | | | | |
| 100 μg/mL | 28.78 | 29.87 | 29.56 | 29.4 | 0.56 | 0.32 |
| 250 μg/mL | 28.77 | 29.77 | 29.78 | 29.44 | 0.58 | 0.34 |
| LSC, t = 24 | | | | | | |
| 100 μg/mL | 27.65 | 27.16 | 27.89 | 27.57 | 0.37 | 0.21 |
| 250 μg/mL | 24.32 | 24.33 | 25.21 | 24.62 | 0.51 | 0.30 |
| LSC diff. | | | | | | |
| 100 μg/mL | 1.13 | 2.71 | 1.67 | 1.84 | 0.66 | 0.38 |
| 250 μg/mL | 4.45 | 5.44 | 4.57 | 4.82 | 0.44 | 0.25 |
| OSC, t = 0 | | | | | | |
| 100 μg/mL | 28.9 | 28.78 | 29 | 28.89 | 0.11 | 0.06 |
| 250 μg/mL | 28.97 | 28.98 | 28.78 | 28.91 | 0.11 | 0.07 |
| OSC, t = 24 | | | | | | |
| 100 μg/mL | 25.43 | 26.21 | 24.43 | 25.36 | 0.89 | 0.52 |
| 250 μg/mL | 24.32 | 24.44 | 23.21 | 23.99 | 0.68 | 0.39 |
| OSC diff. | | | | | | |
| 100 μg/mL | 3.47 | 2.57 | 4.57 | 3.54 | 0.82 | 0.47 |
| 250 μg/mL | 4.65 | 4.54 | 5.57 | 4.92 | 0.46 | 0.27 |

| Treatment | Mean ratio | standard deviation |
|---|---|---|
| AFP | | |
| 100 μg/mL | 1.69 | 0.35 |
| 250 μg/mL | 2.36 | 0.38 |
| DRE | | |
| 100 μg/mL | 1.19 | 0.38 |
| 250 μg/mL | 1.75 | 0.34 |
| AVJ | | |
| 100 μg/mL | 1.49 | 0.35 |
| 250 μg/mL | 1.83 | 0.77 |
| GLE | | |
| 100 μg/mL | 1.16 | 0.50 |
| 250 μg/mL | 2.73 | 0.37 |
| LSC | | |
| 100 μg/mL | 1.01 | 0.48 |
| 250 μg/mL | 2.65 | 0.33 |
| OSC | | |
| 100 μg/mL | 1.94 | 0.39 |
| 250 μg/mL | 2.70 | 0.33 |

Table 5 shows results calculated from the data of from Table 4 where each value was calculated by forming a ratio of the mean differences of Table 4 to the mean differences of the control wells. Standard deviations were calculated by error propagation assuming errors were uncorrelated. These summary results showed a higher degree of scratch closure for the treated wells, with a higher degree of closure at the higher plant material concentrations. The number of replicates may not be sufficient to show reasonable statistical significance for the effects in all cases. AFP, GLE, LSC, and OSC had the most outstanding performance in promoting regeneration under the conditions of this assay. Each of the plant stem cell extracts outperformed all but one of the non-stem-cell materials.

Figure 4:
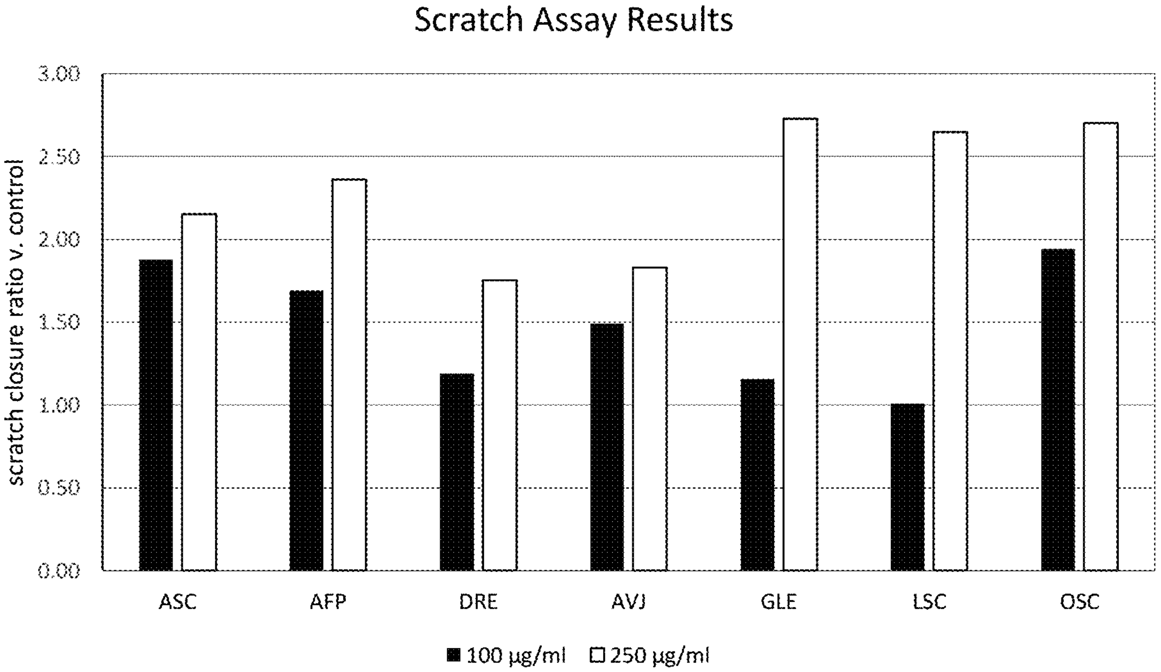
FIG. 4 is a summary graphical representation of control-ratioed scratch assay results exemplified in FIGS. 3A-G.

FIG. 4 is a summary graphical representation of the control-ratioed scratch assay results (including the ASC results from Example 4). Note the consistent values where scratch results for treated cells are greater than one, particularly at the higher tested concentrations, with the higher concentration plant stem cell extracts consistently promoting regeneration in this assay.

Example 6: TNF-α Cytokine Release Assay

In an inflammatory reaction, activated cells (such as macrophages) release a variety of pro-inflammatory cytokines (such as tumor necrosis factor alpha (TNF-α). The released cytokines can be assayed as a measure of inflammatory activity. To evaluate the anti-inflammatory role of apple stem cell extracts, mouse RAW 264.7 cell lines mouse macrophages were used as an adherent monolayer on petri dishes. These cells could be harvested easily without damage caused by enzymes or cell scrapers. The macrophages were stimulated in suspension with lipopolysaccharide (LPS) to initiate an inflammatory response. Cells were seeded into 12-well cell culture plates containing the apple stem cell extract treatment materials. After 16-18 hours, the medium conditioned by the macrophages was harvested and the cytokine profile in the medium determined with enzyme-linked immunosorbent assays (ELISA) by measuring TNF-α levels.

Method: Three concentration of ASC (6.25, 12.5 and 25 μg/mL in media) were tested for the anti-inflammatory effect. RAW 264.7 mouse macrophage cells were maintained in DMEM containing Glutamax supplemented with 10% FBS, penicillin (100 U/ml) and streptomycin (100 μg/ml). The macrophages treated with LPS (1:500 dilution of a 0.1 mg/ml solution of LPS in phosphate buffered saline (PBS)) to produce a pro-inflammatory response. The ASC treatment was performed with a final concentration of $1\times10^5$ macrophages in wells of a 12-well plate. The cytokine assay was performed using a TNF-α ELISA from R&D Systems of Minneapolis, Minnesota.

Figure 5:
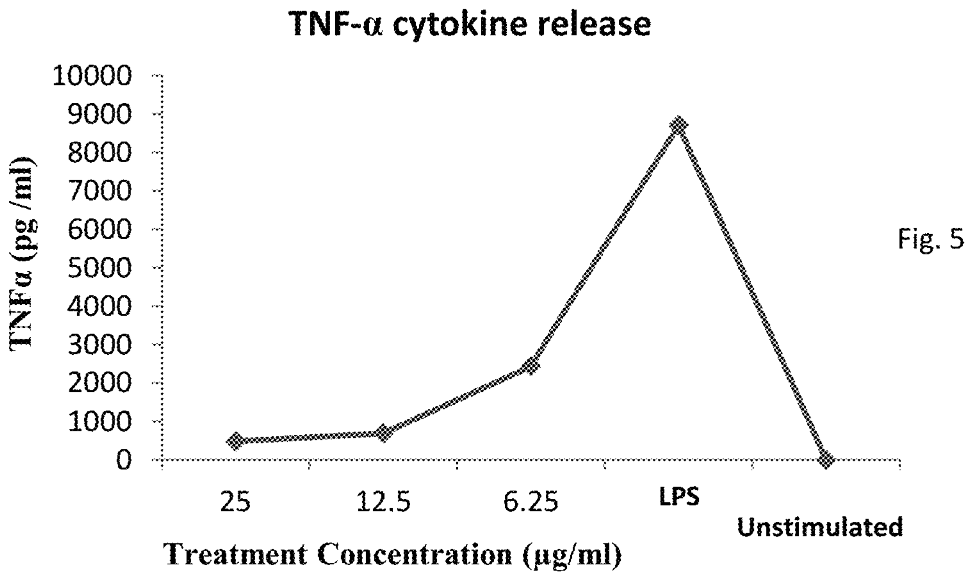
FIG. 5 shows a graph of TNF-α release inflammatory response from stimulated mouse macrophages when treated with an apple stem cell embodiment of the invention.

Results indicated (Table 6, FIG. 5) that LPS alone produced an inflammatory response more than 1000 times that of unstimulated cells as measured by TNF-α expression. Treatment with ASC on the induced macrophages showed a dose-dependent decrease of TNF-α expression. ASC concentrations of 6.25, 12.5, and 25 μg/mL reduced TNF-α activity in the induced cells by 72.1, 92.1 and 94.5%, respectively. This reduced TNF-α at doses of 12.5 and 25 μg/ml was statistically significant with $p\leq0.05$ for 25 μg/ml and $p<0.02$ in 12.5 μg/ml. The apple stem cell extracts thus exerted an anti-inflammatory effect on the activated macrophage cells.

TABLE 6

Results of TNF-α release assay showing anti-inflammatory effects of apple stem cell extracts on mouse RAW 264.7 macrophage cell line cells. Values shown are averages of three sets of experiments. ASC extracts dramatically reduced inflammatory responses in the target cells, as exemplified by reduced TNF-α release (greater inhibition of inflammation).

| Apple Stem Cell Extract Conc. (μg/ml) | TNF-α (pg/ml) | percent inhibition vs. LPS |
|---|---|---|
| 25 | 481.89 | 94.5 |
| 12.5 | 687.9 | 92.1 |
| 6.25 | 2432.89 | 72.1 |
| LPS | 8712.63 | 0 |
| unstimulated | 6.45 | |

Example 7: MTT Cell Proliferation Assay I

The MTT Cell Proliferation assay determines cell survival following apple stem cell extract treatment. The purpose was to evaluate the potential anti-tumor activity of apple stem cell extracts as well as to evaluate the dose-dependent cell cytotoxicity.

Principle: Treated cells are exposed to 3-(4,5-dimethythiazol-2-yl)-2,5-diphenyl tetrazolium bromide (MTT). MTT enters living cells and passes into the mitochondria where it is reduced by mitochondrial succinate dehydrogenase to an insoluble, colored (dark purple) formazan product. The cells are then solubilized with DMSO and the released, solubilized formazan is measured spectrophotometrically. The MTT assay measures cell viability based on the generation of reducing equivalents. Reduction of MTT only occurs in metabolically active cells, so the level of activity is a measure of the viability of the cells. The percentage cell viability is calculated against untreated cells.

Method: A549 and NCI-H520 lung cancer cell lines and L132 lung epithelial cell line were used to determine the plant stem cell treatment tumor-specific cytotoxicity. The cell lines were maintained in Minimal Essential Media supplemented with 10% FBS, penicillin (100 U/ml) and streptomycin (100 μg/ml) in a 5% $CO_2$ at 37 Celsius. Cells were seeded at $5\times10^3$ cells/well in 96-well plates and incubated for 48 hours. Triplicates of eight concentrations of the apple stem cell extract were added to the media and cells were incubated for 24 hours. This was followed by removal of media and subsequent washing with the phosphate saline solution. Cell proliferation was measured using the MTT Cell Proliferation Kit I (Boehringer Mannheim, Indianapolis, IN). New medium containing 50 μl of MTT solution (5 mg/ml) was added to each well and cultures were incubated a further 4 hours. Following this incubation, DMSO was added and the cell viability was determined by the absorbance at 570 nm by a microplate reader.

In order to determine the effectiveness of apple stem cell extracts as an anti-tumor biological agent, an MTT assay was carried out and IC50 values were calculated. IC50 is the half maximal inhibitory function concentration of a drug or compound required to inhibit a biological process. The measured process is cell death.

Results: ASC-treated Human lung adenocarcinoma cell line A549.

TABLE 7

Results of cytotoxicity of apple stem cell extract on lung cancer cell line A549 as measured by MTT assay (performed in triplicate). Values of replicates are % of cell death.

| Concentration* (μg/ml) | replicate 1 | replicate 2 | replicate 3 | Mean of replicates | SD | SEM | % Live Cells |
|---|---|---|---|---|---|---|---|
| 250 | 93.18 | 90.86 | 90.34 | 91.46 | 1.51 | 0.87 | 8.54 |
| 100 | 86.88 | 85.18 | 85.69 | 85.92 | 0.87 | 0.50 | 14.08 |
| 50 | 80.58 | 79.49 | 81.04 | 80.37 | 0.80 | 0.46 | 19.63 |
| 25 | 74.28 | 73.81 | 76.39 | 74.83 | 1.38 | 0.79 | 25.17 |
| 12.5 | 67.98 | 68.13 | 71.75 | 69.28 | 2.13 | 1.23 | 30.72 |
| 6.25 | 61.67 | 62.45 | 67.10 | 63.74 | 2.93 | 1.69 | 36.26 |
| 3.125 | 55.37 | 56.77 | 62.45 | 58.20 | 3.75 | 2.16 | 41.80 |
| 1.562 | 49.07 | 51.08 | 57.80 | 52.65 | 4.57 | 2.64 | 47.35 |
| 0.781 | 42.77 | 45.40 | 53.15 | 47.11 | 5.40 | 3.12 | 52.89 |

Results: ASC-treated Human squamous carcinoma cell line NCI-H520.

TABLE 8

Results of cytotoxicity of apple stem cell extract on lung cancer cell line NCI-H520 measured by MTT assay (performed in triplicate). Values of replicates are % of cell death.

| Concentration* (μg/ml) | replicate 1 | replicate 2 | replicate 3 | Mean of replicates | SD | SEM | % Live cell |
|---|---|---|---|---|---|---|---|
| 250 | 88.28 | 89.29 | 87.73 | 88.43 | 0.79 | 0.46 | 11.57 |
| 100 | 78.13 | 79.19 | 78.13 | 78.48 | 0.61 | 0.35 | 21.52 |
| 50 | 67.98 | 69.09 | 68.54 | 68.54 | 0.56 | 0.32 | 31.46 |
| 25 | 57.83 | 58.99 | 58.94 | 58.59 | 0.66 | 0.38 | 41.41 |
| 12.5 | 47.68 | 48.89 | 49.34 | 48.64 | 0.86 | 0.50 | 51.36 |
| 6.25 | 37.53 | 38.79 | 39.75 | 38.69 | 1.11 | 0.64 | 61.31 |
| 3.125 | 27.37 | 28.69 | 30.15 | 28.74 | 1.39 | 0.80 | 71.26 |
| 1.562 | 17.22 | 18.59 | 20.56 | 18.79 | 1.68 | 0.97 | 81.21 |
| 0.781 | 7.07 | 8.48 | 10.96 | 8.84 | 1.97 | 1.14 | 91.16 |

Results: ASC-treated lung epithelial cell line L132.

TABLE 9

Results of cytotoxicity of apple stem cell extract on lung epithelial cell line L132 as measured by MTT assay (performed in triplicate). Values of replicates are % of cell death.

| Concentration* (μg/ml) | replicate 1 | replicate 2 | replicate 3 | Mean of replicates | SD | SEM | % Live cell |
|---|---|---|---|---|---|---|---|
| 250 | 39.51 | 42.52 | 44.03 | 42.02 | 2.30 | 1.33 | 57.98 |
| 100 | 32.93 | 34.44 | 33.69 | 33.69 | 0.75 | 0.44 | 66.31 |
| 50 | 30.60 | 28.94 | 30.52 | 30.02 | 0.94 | 0.54 | 69.98 |
| 25 | 27.96 | 27.81 | 27.13 | 27.63 | 0.44 | 0.25 | 72.37 |
| 12.5 | 25.62 | 25.55 | 25.40 | 25.52 | 0.12 | 0.07 | 74.48 |
| 6.25 | 23.13 | 20.87 | 18.61 | 20.87 | 2.26 | 1.31 | 79.13 |
| 3.125 | 13.34 | 11.08 | 11.83 | 12.08 | 1.15 | 0.66 | 87.92 |
| 1.562 | 6.56 | 7.31 | 9.57 | 7.81 | 1.57 | 0.91 | 92.19 |
| 0.781 | 8.06 | 4.30 | 3.54 | 5.30 | 2.42 | 1.40 | 94.70 |

Summary Results: cytotoxicity of apple stem cell extracts.

TABLE 10

IC50 values of the apple stem cell extracts on the on the target cell lines as determined by MTT assay.

| Target Cell Line | IC50 |
|---|---|
| A549 | 12.58 |
| NCI-H520 | 10.21 |
| L132 | 127.46 |

Figure 6:
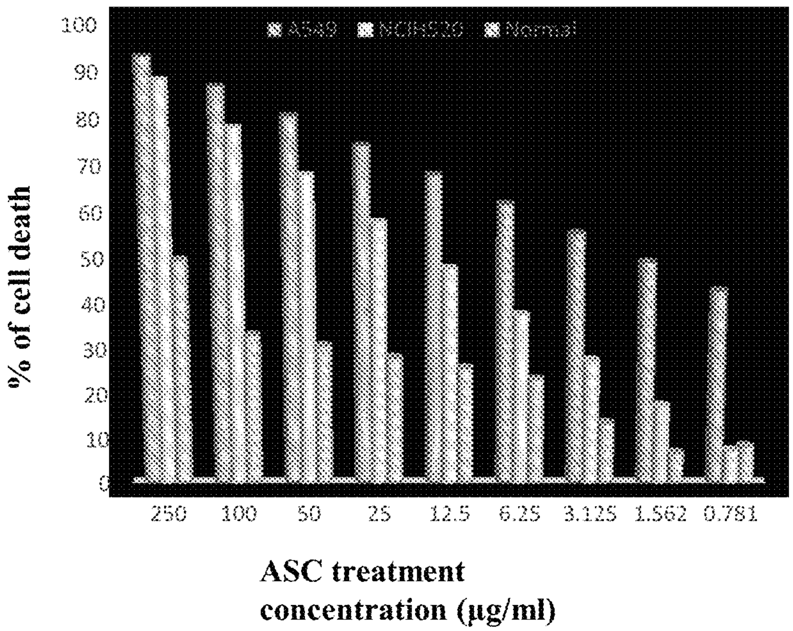
FIG. 6 shows a graph of cytotoxicity activity of an apple stem cell embodiment of the invention on lung tumor cell lines A549 and NCIH520 and on a lung epithelial cell line.

Apple stem cell extracts killed lung cancer cells lines A549 and NCI-H520 at relatively low doses: IC50s were 12.58 and 10.21 μg/ml respectively as compared to 127.46 μg/ml for the lung epithelial cell line L132. Near complete anti-tumor activity was seen at a dose of 250 μg/ml in both the lung cancer cell lines. This same dose spared more than one half of the L132 cells. See Tables 7-10. The data revealed that apple stem cell extract is cytotoxic to lung cancer cells while sparing lung epithelial cells. FIG. 6 shows a graphical representation of cytotoxicity activity of apple stem cell extracts on lung tumor cell lines A549, NCIH520 and on L132 lung epithelial cell line (marked "Normal"). The Y-axis is the mean % of cells killed by the indicated treatment compared to unexposed cells. The difference in cytotoxicity levels was statistically significant at $p \leq 0.05$.

Example 9: MTT Cell Proliferation Assay II

The experiment of Example 7 was repeated substituting other plant materials for ASC. Plant stem cell materials included Dandelion Root Extract (DRE), Aloe Vera Juice (AVJ), Apple Fiber Powder (AFP), *Ginkgo* Leaf Extract (GLE), Lingonberry Stem Cells (LSC), Orchid Stem Cells (OSC) as described in Examples 1 and 2. The concentrations of plant materials used were nominally 250, 100, 50, 25, 6.25, 3.125, 1.562, and 0.781 μg/mL. These materials were tested only for cells the human lung epithelial cell line L132 (as a proxy for normal epithelial cells) and for cells of the human lung adenocarcinoma cell line A549 (as a proxy for lung cancer cells).

A549 cells lung cancer cell line cytotoxicity results for each of the treatment materials.

DRE-treated lung cancer cell line A549 cells.

TABLE 11

Triplicate results of cell death of DRE-treated A549 cells measured by MTT assay. Percentage of live cells calculated as 100% − Mean of triplicates.

| Concentration (μg/mL)-DRE-treated A549 | % of cell death | | | Mean | SD | SEM | % Live cell |
|---|---|---|---|---|---|---|---|
| 250 | 80.43 | 76.40 | 74.84 | 77.23 | 2.89 | 1.67 | 22.77 |
| 100 | 67.60 | 75.26 | 63.77 | 68.88 | 5.85 | 3.38 | 31.12 |
| 50 | 65.32 | 62.94 | 59.94 | 62.73 | 2.70 | 1.56 | 37.27 |
| 25 | 56.83 | 57.97 | 48.14 | 54.31 | 5.38 | 3.11 | 45.69 |
| 6.25 | 55.59 | 49.69 | 49.17 | 51.48 | 3.57 | 2.06 | 48.52 |
| 3.125 | 51.76 | 48.45 | 45.34 | 48.52 | 3.21 | 1.85 | 51.48 |
| 1.562 | 43.69 | 44.00 | 36.02 | 41.24 | 4.52 | 2.61 | 58.76 |
| 0.781 | 37.47 | 26.19 | 19.57 | 27.74 | 9.05 | 5.23 | 72.26 |

AVJ-treated lung cancer cell line A549 cells.

TABLE 12

Triplicate results of cell death of AVJ-treated A549 cells measured by MTT assay. Percentage of live cells calculated as 100% − Mean of triplicates.

| Concentration (μg/mL)-AVJ-treated A549 | % of cell death | | | Mean | SD | SEM | % Live cell |
|---|---|---|---|---|---|---|---|
| 250 | 76.81 | 78.16 | 75.88 | 76.95 | 1.14 | 0.66 | 23.05 |
| 100 | 76.40 | 75.26 | 73.71 | 75.12 | 1.35 | 0.78 | 24.88 |
| 50 | 65.32 | 66.15 | 59.94 | 63.80 | 3.37 | 1.95 | 36.20 |
| 25 | 50.10 | 48.45 | 56.63 | 51.73 | 4.32 | 2.50 | 48.27 |
| 6.25 | 47.52 | 46.38 | 46.17 | 46.69 | 0.72 | 0.42 | 53.31 |
| 3.125 | 39.86 | 38.61 | 43.79 | 40.75 | 2.70 | 1.56 | 59.25 |
| 1.562 | 32.40 | 19.77 | 30.54 | 27.57 | 6.82 | 3.94 | 72.43 |
| 0.781 | 20.50 | 15.63 | 32.19 | 22.77 | 8.51 | 4.92 | 77.23 |

AFP-treated lung cancer cell line A549 cells.

TABLE 13

Triplicate results of cell death of AFP-treated A549 cells measured by MTT assay. Percentage of live cells calculated as 100% − Mean of triplicates.

| Concentration (μg/mL)-AFP-treated A549 | % of cell death | | | Mean | SD | SEM | % Live cell |
|---|---|---|---|---|---|---|---|
| 250 | 86.13 | 87.99 | 86.65 | 86.92 | 0.96 | 0.56 | 13.08 |
| 100 | 79.50 | 81.06 | 82.09 | 80.88 | 1.30 | 0.75 | 19.12 |
| 50 | 73.60 | 72.46 | 71.33 | 72.46 | 1.14 | 0.66 | 27.54 |
| 25 | 68.01 | 67.70 | 66.98 | 67.56 | 0.53 | 0.31 | 32.44 |
| 6.25 | 60.87 | 62.11 | 60.77 | 61.25 | 0.75 | 0.43 | 38.75 |
| 3.125 | 49.48 | 51.76 | 50.72 | 50.66 | 1.14 | 0.66 | 49.34 |
| 1.562 | 40.06 | 41.72 | 47.00 | 42.93 | 3.62 | 2.09 | 57.07 |
| 0.781 | 39.23 | 37.78 | 36.85 | 37.96 | 1.20 | 0.69 | 62.04 |

GLE-treated lung cancer cell line A549 cells.

TABLE 14

Triplicate results of cell death of GLE-treated A549 cells measured by MTT assay. Percentage of live cells calculated as 100% − Mean of triplicates.

| Concentration (μg/mL)-GLE-treated A549 | % of cell death | | | Mean | SD | SEM | % Live cell |
|---|---|---|---|---|---|---|---|
| 250 | 88.42 | 91.49 | 90.44 | 90.12 | 1.56 | 0.90 | 9.88 |
| 100 | 84.39 | 83.77 | 83.16 | 83.77 | 0.61 | 0.35 | 16.23 |
| 50 | 79.47 | 81.58 | 76.75 | 79.27 | 2.42 | 1.40 | 20.73 |
| 25 | 73.60 | 72.54 | 71.40 | 72.51 | 1.10 | 0.63 | 27.49 |
| 6.25 | 62.89 | 63.68 | 59.91 | 62.16 | 1.99 | 1.15 | 37.84 |
| 3.125 | 50.18 | 54.47 | 51.84 | 52.16 | 2.17 | 1.25 | 47.84 |
| 1.562 | 46.93 | 44.30 | 43.33 | 44.85 | 1.86 | 1.07 | 55.15 |
| 0.781 | 39.56 | 39.39 | 40.96 | 39.97 | 0.87 | 0.50 | 60.03 |

LSC-treated lung cancer cell line A549 cells.

TABLE 15

Triplicate results of cell death of LSC-treated A549 cells measured by MTT assay. Percentage of live cells calculated as 100% − Mean of triplicates.

| Concentration (μg/mL) LSC treated A549 | % of cell death | | | Mean | SD | SEM | % Live cell |
|---|---|---|---|---|---|---|---|
| 250 | 77.54 | 78.85 | 78.20 | 78.20 | 0.65 | 0.38 | 21.80 |
| 100 | 77.14 | 76.04 | 76.59 | 76.59 | 0.55 | 0.32 | 23.41 |
| 50 | 66.42 | 68.52 | 66.82 | 67.25 | 1.12 | 0.65 | 32.75 |
| 25 | 59.80 | 67.22 | 64.16 | 63.73 | 3.73 | 2.15 | 36.27 |
| 6.25 | 50.53 | 48.82 | 48.07 | 49.14 | 1.26 | 0.73 | 50.86 |
| 3.125 | 41.14 | 43.60 | 42.72 | 42.49 | 1.24 | 0.72 | 57.51 |
| 1.562 | 39.47 | 39.74 | 40.61 | 39.94 | 0.60 | 0.34 | 60.06 |
| 0.781 | 38.55 | 31.83 | 36.79 | 35.72 | 3.48 | 2.01 | 64.28 |

OSC-treated lung cancer cell line A549 cells.

TABLE 16

Triplicate results of cell death of OSC-treated A549 cells measured by MTT assay. Percentage of live cells calculated as 100% − Mean of triplicates.

| Concentration (μg/mL) OSC-treated A549 | % of cell death | | | Mean | SD | SEM | % Live cell |
|---|---|---|---|---|---|---|---|
| 250 | 70.84 | 65.57 | 71.49 | 69.30 | 3.25 | 1.87 | 30.70 |
| 100 | 48.81 | 50.91 | 57.28 | 52.33 | 4.41 | 2.55 | 47.67 |
| 50 | 46.59 | 49.60 | 53.33 | 49.84 | 3.38 | 1.95 | 50.16 |
| 25 | 38.77 | 40.81 | 36.58 | 38.72 | 2.11 | 1.22 | 61.28 |
| 6.25 | 35.74 | 40.79 | 41.05 | 39.19 | 3.00 | 1.73 | 60.81 |
| 3.125 | 34.55 | 33.68 | 37.02 | 35.08 | 1.73 | 1.00 | 64.92 |
| 1.562 | 33.86 | 33.44 | 27.63 | 31.64 | 3.48 | 2.01 | 68.36 |
| 0.781 | 21.32 | 20.00 | 34.82 | 25.38 | 8.21 | 4.74 | 74.62 |

L132 cells ("normal" lung epithelial cell line) cytotoxicity results for each of the treatment materials.

DRE-treated lung epithelial cell line L132 cells.

TABLE 17

Triplicate results of cell death of DRE-treated L132 cells measured by MTT assay. Percentage of live cells calculated as 100% − Mean of triplicates.

| Concentration (μg/mL) DRE-treated L132 | % of cell death | | | Mean | SD | SEM | % Live cell |
|---|---|---|---|---|---|---|---|
| 250 | 86.66 | 86.61 | 86.66 | 86.64 | 0.03 | 0.02 | 13.36 |
| 100 | 76.29 | 77.39 | 76.84 | 76.84 | 0.55 | 0.32 | 23.16 |
| 50 | 65.92 | 68.17 | 67.01 | 67.03 | 1.13 | 0.65 | 32.97 |
| 25 | 55.54 | 58.95 | 57.19 | 57.23 | 1.70 | 0.98 | 42.77 |
| 6.25 | 45.17 | 49.73 | 47.37 | 47.42 | 2.28 | 1.32 | 52.58 |
| 3.125 | 34.80 | 40.50 | 37.54 | 37.61 | 2.85 | 1.65 | 62.39 |
| 1.562 | 24.42 | 31.28 | 27.72 | 27.81 | 3.43 | 1.98 | 72.19 |
| 0.781 | 14.05 | 22.06 | 17.89 | 18.00 | 4.01 | 2.31 | 82.00 |

AVJ-treated lung epithelial cell line L132 cells.

TABLE 18

Triplicate results of cell death of AVJ-treated L132 cells measured by MTT assay. Percentage of live cells calculated as 100% − Mean of triplicates AFP-treated lung epithelial cell line L132 cells.

| Concentration (μg/mL) AVJ-treated L132 | % of cell death | | | Mean | SD | SEM | % Live cell |
|---|---|---|---|---|---|---|---|
| 250 | 57.03 | 55.93 | 53.62 | 55.53 | 1.74 | 1.00 | 44.47 |
| 100 | 50.99 | 49.78 | 47.04 | 49.27 | 2.03 | 1.17 | 50.73 |
| 50 | 44.95 | 43.63 | 40.45 | 43.01 | 2.31 | 1.34 | 56.99 |
| 25 | 38.91 | 37.49 | 33.86 | 36.75 | 2.60 | 1.50 | 63.25 |
| 6.25 | 32.88 | 31.34 | 27.28 | 30.50 | 2.89 | 1.67 | 69.50 |
| 3.125 | 26.84 | 25.19 | 20.69 | 24.24 | 3.18 | 1.84 | 75.76 |
| 1.562 | 20.80 | 19.05 | 14.11 | 17.98 | 3.47 | 2.00 | 82.02 |
| 0.781 | 14.76 | 12.90 | 7.52 | 11.73 | 3.76 | 2.17 | 88.27 |

AFP-treated lung epithelial cell line L132 cells.

TABLE 19

Triplicate results of cell death of AFP-treated L132 cells measured by MTT assay. Percentage of live cells calculated as 100% − Mean of triplicates AFP-treated lung epithelial cell line L132 cells.

| Concentration (μg/mL) AFP-treated L132 | % of cell death | | | Mean | SD | SEM | % Live cell |
|---|---|---|---|---|---|---|---|
| 250 | 56.15 | 55.43 | 57.19 | 56.26 | 0.88 | 0.51 | 43.74 |
| 100 | 49.95 | 48.24 | 47.64 | 48.61 | 1.20 | 0.69 | 51.39 |
| 50 | 43.74 | 41.05 | 38.09 | 40.96 | 2.83 | 1.63 | 59.04 |
| 25 | 37.54 | 33.86 | 28.54 | 33.32 | 4.53 | 2.61 | 66.68 |
| 6.25 | 31.34 | 26.67 | 18.99 | 25.67 | 6.24 | 3.60 | 74.33 |
| 3.125 | 25.14 | 19.48 | 9.44 | 18.02 | 7.95 | 4.59 | 81.98 |
| 1.562 | 18.94 | 12.29 | 10.87 | 14.03 | 4.31 | 2.49 | 85.97 |
| 0.781 | 12.73 | 5.10 | 6.81 | 8.21 | 4.00 | 2.31 | 91.79 |

GLE-treated lung epithelial cell line L132 cells.

TABLE 20

Triplicate results of cell death of GLE-treated L132 cells measured by MTT assay. Percentage of live cells calculated as 100% − Mean of triplicates AFP-treated lung epithelial cell line L132 cells.

| Concentration (μg/mL) GLE-treated L132 | % of cell death | | | Mean | SD | SEM | % Live cell |
|---|---|---|---|---|---|---|---|
| 250 | 84.42 | 83.20 | 83.08 | 83.57 | 0.74 | 0.43 | 16.43 |
| 100 | 80.05 | 79.29 | 78.59 | 79.31 | 0.73 | 0.42 | 20.69 |
| 50 | 72.75 | 71.59 | 74.10 | 72.81 | 1.26 | 0.72 | 27.19 |
| 25 | 80.05 | 81.86 | 79.99 | 80.63 | 1.06 | 0.61 | 19.37 |
| 6.25 | 68.26 | 70.13 | 68.26 | 68.88 | 1.08 | 0.62 | 31.12 |
| 3.125 | 60.62 | 63.07 | 60.62 | 61.44 | 1.41 | 0.82 | 38.56 |
| 1.562 | 48.07 | 48.77 | 48.83 | 48.56 | 0.42 | 0.24 | 51.44 |
| 0.781 | 46.27 | 45.57 | 46.67 | 46.17 | 0.56 | 0.32 | 53.83 |

LSC-treated lung epithelial cell line L132 cells.

TABLE 21

Triplicate results of cell death of LSC-treated L132 cells measured by MTT assay. Percentage of live cells calculated as 100% − Mean of triplicates AFP-treated lung epithelial cell line L132 cells.

| Concentration (μg/mL) LSC-treated L132 | % of cell death | | | Mean | SD | SEM | % Live cell |
|---|---|---|---|---|---|---|---|
| 250 | 86.41 | 85.82 | 85.76 | 86.00 | 0.35 | 0.20 | 14.00 |
| 100 | 81.21 | 81.27 | 79.99 | 80.82 | 0.72 | 0.42 | 19.18 |
| 50 | 75.96 | 74.74 | 73.51 | 74.74 | 1.23 | 0.71 | 25.26 |
| 25 | 74.74 | 72.75 | 71.47 | 72.99 | 1.65 | 0.95 | 27.01 |
| 6.25 | 70.13 | 68.32 | 68.26 | 68.90 | 1.06 | 0.61 | 31.10 |
| 3.125 | 54.03 | 58.05 | 53.44 | 55.17 | 2.51 | 1.45 | 44.83 |
| 1.562 | 53.97 | 51.98 | 51.98 | 52.64 | 1.15 | 0.66 | 47.36 |
| 0.781 | 46.79 | 45.62 | 44.92 | 45.78 | 0.94 | 0.54 | 54.22 |

OSC-treated lung epithelial cell line L132 cells.

TABLE 22

Triplicate results of cell death of OSC-treated L132 cells measured by MTT assay. Percentage of live cells calculated as 100% − Mean of triplicates AFP-treated lung epithelial cell line L132 cells.

| Concentration (μg/mL) OSC-treated L132 | % of cell death | | | Mean | SD | SEM | % Live cell |
|---|---|---|---|---|---|---|---|
| 250 | 61.84 | 62.37 | 60.44 | 61.55 | 1.00 | 0.57 | 38.45 |
| 100 | 54.14 | 53.44 | 52.10 | 53.23 | 1.04 | 0.60 | 46.77 |
| 50 | 42.94 | 42.30 | 40.32 | 41.85 | 1.37 | 0.79 | 58.15 |
| 25 | 35.94 | 34.48 | 33.31 | 34.58 | 1.32 | 0.76 | 65.42 |
| 6.25 | 33.96 | 32.67 | 32.03 | 32.89 | 0.98 | 0.57 | 67.11 |
| 3.125 | 27.48 | 26.20 | 26.72 | 26.80 | 0.65 | 0.37 | 73.20 |
| 1.562 | 9.80 | 7.29 | 7.35 | 8.15 | 1.43 | 0.83 | 91.85 |
| 0.781 | 7.29 | 8.98 | 8.05 | 8.11 | 0.85 | 0.49 | 91.89 |

Calculated values.

TABLE 23

Calculated IC50 doses (ug/mL) and therapeutic ratios (IC50 for L132 cells/IC50 for A549 cells) for each treatment material. Values greater than one indicate that a material would be more selective in killing cancer cells than normal cells. ASC results imported from Example 8. These studies indicate that at least some of the materials may be effective anti-cancer agents. ASC has outstanding selectivity compared to other materials.

| | ASC | DRE | AVJ | AFP | GLE | LSC | OSC |
|---|---|---|---|---|---|---|---|
| A549 IC50 | 12.58 | 9.822 | 11.48 | 11.98 | 11.1 | 13.7 | 33.9 |
| L132 IC50 | 127.46 | 56.88 | 62.66 | 82.65 | 77.636 | 9.267 | 15.38 |
| Ther. Ratio | 10.1 | 5.8 | 5.5 | 6.9 | 7.0 | 0.7 | 0.5 |

Example 10: Staining of Cells

Apoptosis is a programmed cell death that eliminating physiologically redundant, physically damaged, and abnormal cells. Various staining procedures can help elucidate the mechanisms of cytotoxic effects, and in particular whether cytotoxic effects are attributable to apoptosis as compared to purely physical effects.

Ethidium bromide and acridine orange are used to visualize the cell apoptosis in a cell culture upon treatment with a biological agent or a drug. Acridine orange is a vital dye and will stain both live and dead cells. Ethidium bromide will stain only cells that have lost membrane integrity. Live cells will appear uniformly green. Early apoptotic cells will stain green and contain bright green dots in the nuclei as a consequence of chromatin condensation and nuclear fragmentation. Late apoptotic cells will also incorporate ethidium bromide and therefore stain orange, but, in contrast to necrotic cells, the late apoptotic cells will show condensed and often fragmented nuclei. Necrotic cells stain orange, but have a nuclear morphology resembling that of viable cells, with no condensed chromatin.

Calcein AM staining helps confirm cell viability. Calcein AM is a non-fluorescent, hydrophobic compound that easily permeates intact, live cells. In live cells the nonfluorescent calcein AM is converted to a green-fluorescent calcein after acetoxymethyl ester hydrolysis by intracellular esterases.

Method: A549 and NCI-H520 lung cancer cell lines were cultured in DMEM supplemented with 10% FBS, 4 mM L-glutamine, 1% penicillin/streptomycin under a fully humidified atmosphere containing 5% $CO_2$ at 37 Celsius. For experiments, cells were collected from sub confluent monolayers by trypsinization with trypsin/EDTA. Cell viability was determined using trypan blue dye exclusion staining. In all experiments. Apple stem cell extracts (6.25, 12.5, and 25 μg/mL) and 0.1% DMSO vehicle controls were sterilized with UV and placed in wells of 6 well plates. Culture medium containing A549 or NCI-H520 cells were added and incubated according to the protocols below.

Calcein AM staining: The control and treated cells ($1\times10^5$ per well) were incubated with the apple stem cell extracts for 24 hours at 37 Celsius and 5% $CO_2$. The culture media was aspirated off followed by cell washing with ice cold PBS. 2 μM Calcein-AM and was added and cells incubated for 10 min at 37 Celsius. Cells were examined under a fluorescence microscope provided with a triple filter set (excitation: 400, 495, 570 nm; emission: 460, 530, 610 nm), and combined with digital camera (Canon PowerShot G8). Viability was expressed as percentage cells retaining calcein (green fluorescence) compared to the total cells counted.

Acridine orange/ethidium bromide (AO/EtBr) Staining: The control and treated cells ($3\times10^4$ per well) were incubated with the apple stem cell extracts for 48 hours at 37 Celsius and 5% $CO_2$. After incubation, cells were fixed in methanol: glacial acetic acid (3:1) for 30 min at room temperature, washed with PBS and stained with 1:1 ratio of AO/EtBr. Stained cells were immediately washed with PBS and viewed under a fluorescence microscope (Nikon, Eclipse TS100, Japan) with a magnification of ×40.

The number of cells expressing apoptotic features was counted and expressed as a fraction of the total number of cells present in the field.

Figure 7:
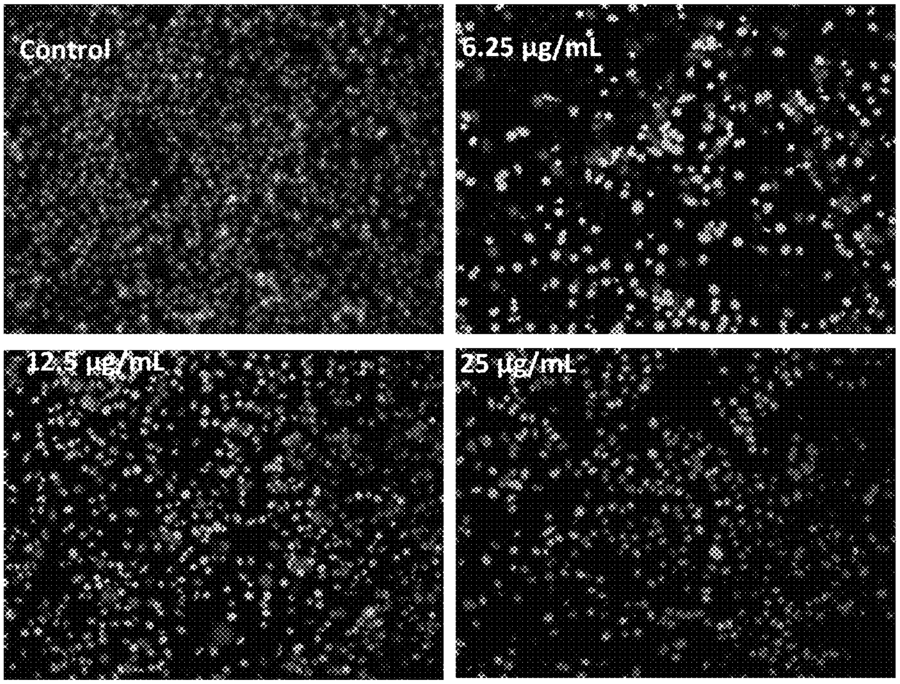
FIG. 7 shows fluorescence micrographs of acridine orange/ethidium bromide staining of A549 cells treated with an apple stem cell embodiment of the invention.
Figure 8:
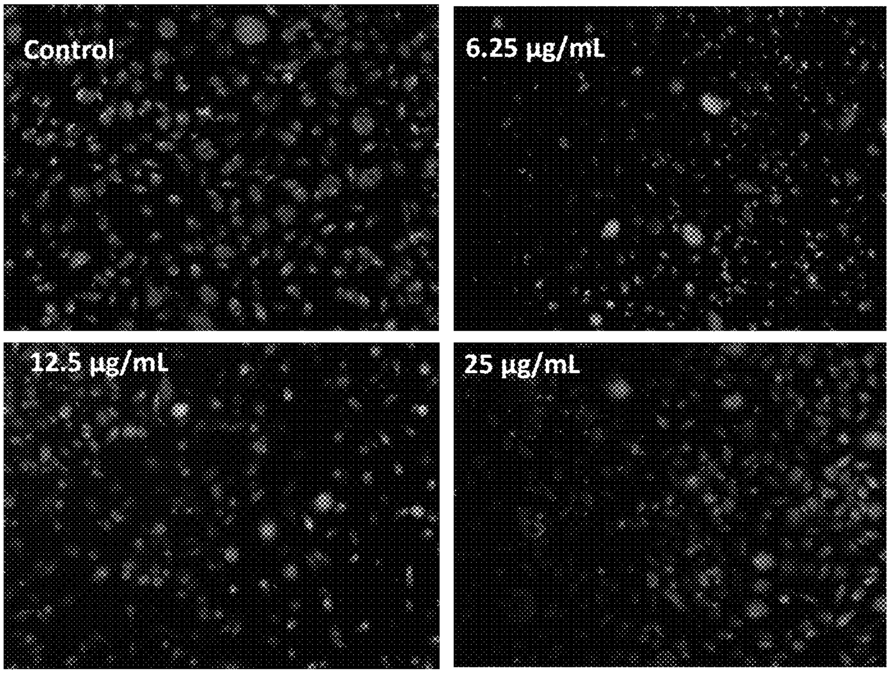
FIG. 8 shows fluorescence micrographs of acridine orange/ethidium bromide staining of NCI-H520 cells treated with an apple stem cell embodiment of the invention.

Results: FIGS. 7-8 show selected fields of treated cells stained with AO/EtBr. These are shown in color to better visualize the distribution of the two stains. Each field has the associated apple stem cell extract treatment dose indicated in the corner. Note that magnification changes between images to better indicate the relative number of cells. Normal tumor cells, early and late apoptotic cells, and necrotic cells were examined using fluorescent microscopy. Early-stage apoptotic cells were marked by crescent-shaped or granular yellow-green acridine orange nuclear staining. Late-stage apoptotic cells were marked with concentrated and asymmetrically localized orange nuclear ethidium bromide staining. Necrotic cells increased in volume and showed uneven orange-red fluorescence at their periphery. Cells appeared to be in the process of disintegrating.

The percentage of apoptotic lung cancer cells of both cell lines detected by AO/EtBr staining was significant at 12.5 μg/ml of treatment dose of apple stem cell extract.

Figure 9:
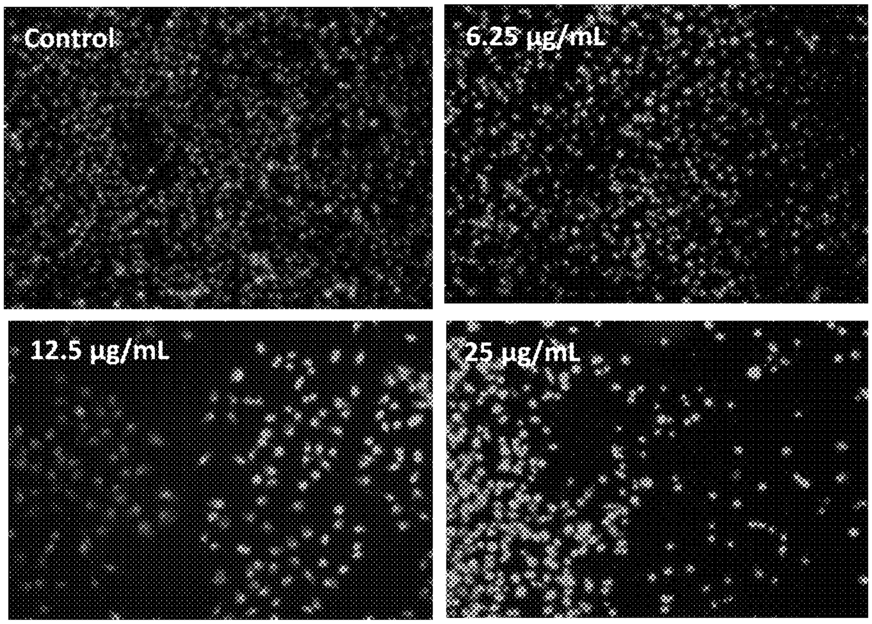
FIG. 9 shows fluorescence micrographs of Calcein AM staining in A549 Lung Cancer Cell Line cells treated with an apple stem cell embodiment of the invention.
Figure 10:
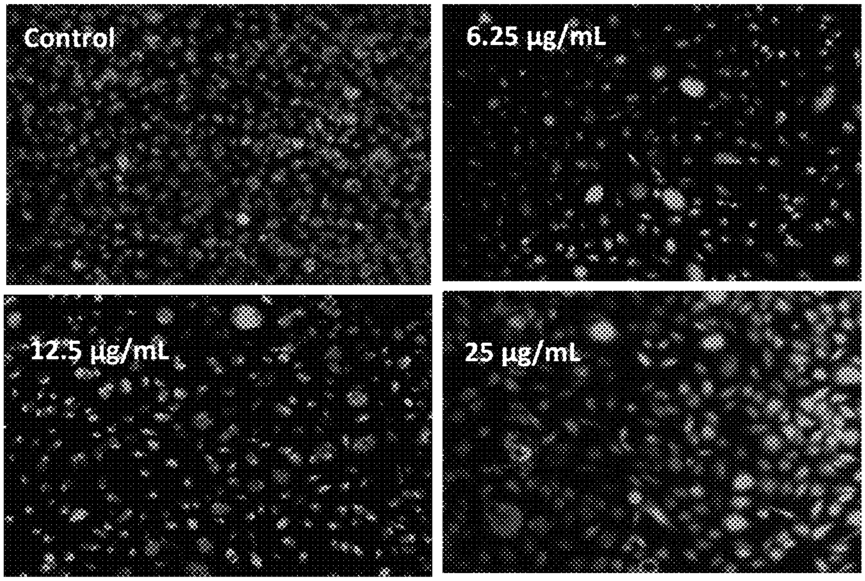
FIG. 10 shows fluorescence micrographs of Calcein AM staining in NCI-H520 Lung Cancer Cell Line cells treated with an apple stem cell embodiment of the plant stem cell of the invention.

FIGS. 9-10 show selected fields of treated cells stained with Calcein AM. Each field has the associated apple stem cell extract treatment dose indicated in the corner. Note that magnification changes between images to better indicate the relative number of cells.

Consistent with the AO/EtBr staining, a dose of 12.5 μg/ml was associated with significantly fewer tumor cells exhibiting the green fluorescence indicative of viable target cells when treated with apple stem cell extract and stained with Calcein-AM. Response to the apple stem cell extracts was dose-dependent; more viable target cells were present in wells treated with lower doses of apple stem cell extracts.

These AO/EtBr and Calcein-AM staining results support that treatment with apple stem cell extracts produces apoptosis and bio-sensitivity in lung tumor cell lines.

Example 11: Lactate Dehydrogenase (LDH) Release Assay

LDH is released upon tumor cell death. Measuring released LDH can confirm cytotoxic effects. LDH is a stable cytosolic enzyme that is released from the cell upon cell lysis. The LDH assay is based on quantitatively measuring released LDH using a coupled enzymatic assay. Released LDH converts a tetrazolium salt into a red soluble formazan product which then can be measured colorimetrically. The amount of LDH released is proportional to the number of lysed cells.

Method: A549 and NCI-H520 cells were cultured as described in Example 5 and treated with varying concentrations of apple stem cell extract (0.781, 1.562, 3.125.6.25.12.5, 25, 50, 100, and 250 μg/ml) of Example 1. The cells were treated at 37 Celsius for 45-60 min, then the supernatant containing released LDH was harvested and transferred into a fresh 96-well plate. 50 μL of substrate mix was added to each well containing the transferred supernatant. The plate was incubated for 30 min at room temperature and the reaction stopped by adding 50 μL of stop solution to each well. Absorbance of the solutions was measured at 490 nm in a plate reader and the results expressed as a percentage of LDH released (n=4±S.D.) compared to maximum LDH released from lysed control cells.

Figure 11:
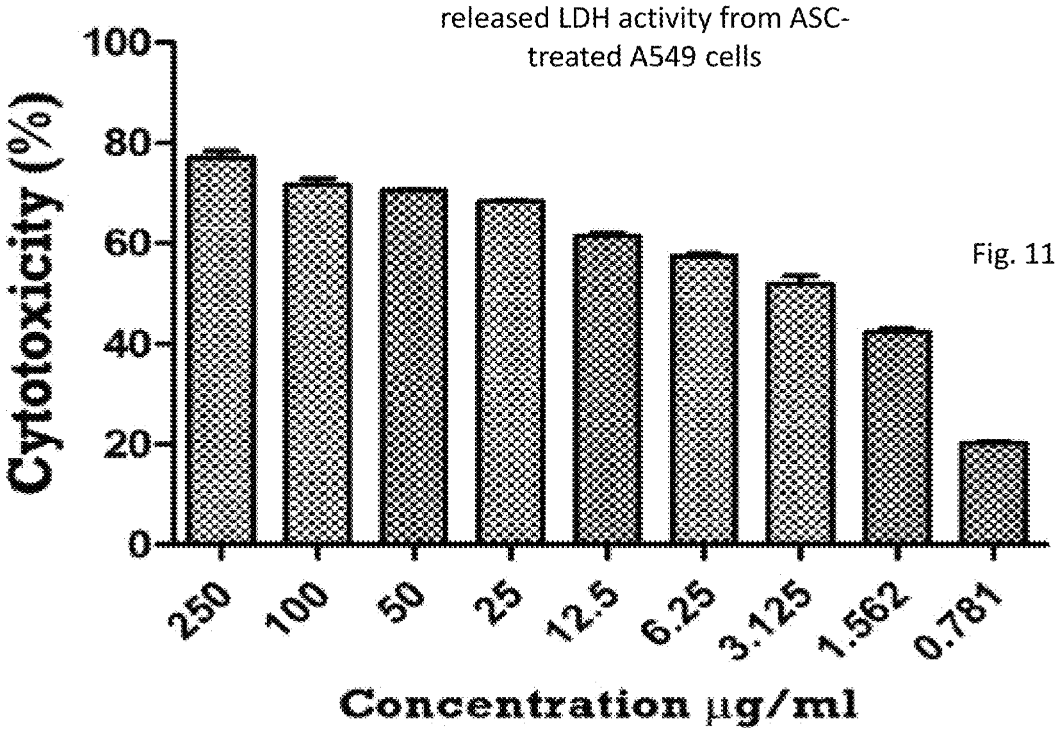
FIG. 11 shows a graph of cytotoxicity activity of an apple stem cell embodiment of the invention on lung tumor cell lines A549 as measured by lactate dehydrogenase release.
Figure 12:
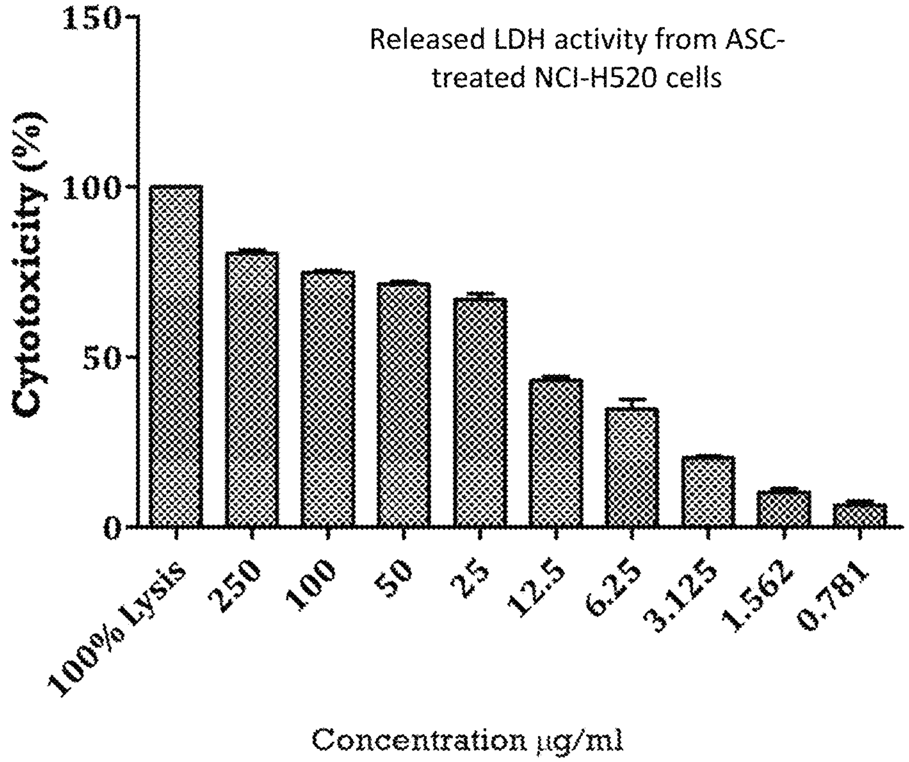
FIG. 12 shows a graph of cytotoxicity activity of an apple stem cell embodiment of the invention on lung tumor cell line NCIH520 and on a lung epithelial cell line as measured by lactate dehydrogenase release.

Results: Significant released LDH activity was observed with doses of 100 and 250 μg/ml correlating to about 78% cell cytotoxicity in both the lung cancer cell lines (FIG. 11 for A549 cells and FIG. 12 for NCI-H520 cells). The data are consistent with the MTT assay results showing anti-tumor cytotoxic action of apple stem cell extract treatments.

Example 12: Antioxidant Activity

The human body both produces and is subject to free radicals. Recovery of injury to any body tissue is frequently manifested by antioxidant enzyme levels. Superoxide anions are produced by dedicated signaling enzymes and as a byproduct of metabolism (e.g. mitochondrial respiration). Inhaled pathogens can also induce airway cells to produce these and other reactive oxidant species (ROS). For example, inhalation of the ubiquitous environmental fungus *Aspergillus fumigatus* can exacerbate airway inflammation. Inhaled ROS and those endogenously formed by inflammatory cells constitute an increased intrapulmonary oxidative burden. Despite their potential toxicity, superoxide ion and some of its derivatives, especially hydrogen peroxide ($H_2O_2$), are also signaling molecules that mediate a variety of biological responses such as cell proliferation, differentiation, and migration. The enzymes involved in repair of free radical-induced DNA damage may be especially important in preventing cancerous transformation.

The balance between oxidants and antioxidants (known as redox balance) is altered in many diseases with severe consequences. The pathophysiological mechanisms by which free radicals generate various types of stress (oxidative stress, nitrative, carbonyl, inflammatory, endoplasmic reticulum stress etc.) culminate in diseases such as chronic obstructive pulmonary disease (COPD), bronchial asthma (BA), bronchiectasis, and idiopathic pulmonary fibrosis (IPF). Studies have shown that there is induction of superoxide dismutase (SOD) and catalase (CAT) during in inflamed tissues generally and in inflammatory lung diseases. The enzymatic induction is responsive to ROS and thus can serve as a proxy for the degree of oxidative stress suffered by the tissue.

The endogenous antioxidant defense system is essential to maintain redox balance. Human tissue produces enzymes that protect against free radicals and ROS. The SOD enzyme helps convert superoxides to $H_2O_2$. $H_2O_2$ may be metabolized by other enzymes such as CAT and glutathione peroxidase. Overexpression of CAT has been associated with impaired post-ischemic neovascularization; this response of elevated antioxidant enzymes, though necessary to combat oxidative stress, has detrimental secondary consequences to tissue recovery and repair.

Measuring the SOD and CAT activities of apple stem cell extracts measures whether the extract exerts an antioxidant function. Lower enzyme activities would indicate that the treated cells have a lower degree of oxidative stress, showing a protective effect from the stem cell treatment.

Method: The SOD assay generates a superoxide radical of riboflavin that reacts with hydroxylamine hydrochloride to form nitrite. The nitrite reacts with sulphanilic acid to produce a diazonium compound which subsequently reacts with naphthylamine to produce a red azo compound with absorbance measured at 543 nm.

CAT is a ubiquitous antioxidant enzyme that degrades hydrogen peroxide into water and oxygen. The CAT assay method is based on the principle that dichromate in acetic acid is reduced to chromic acetate when heated in the presence of $H_2O_2$ with the formation of perchloric acid as an unstable intermediate. The chromic acetate thus produced is measured at 610 nm. Since dichromate has no absorbance in this region, the presence of the compound in the assay mixture did not interfere with the colorimetric determination of chromic acetate. The CAT in the assay preparation was allowed to split $H_2O_2$ for different periods of time. The reaction was stopped at specific time intervals by the addition of dichromate/acetic acid mixture and the remaining $H_2O_2$ was determined by measuring chromic acetate colorimetrically after heating the reaction.

Figure 13:
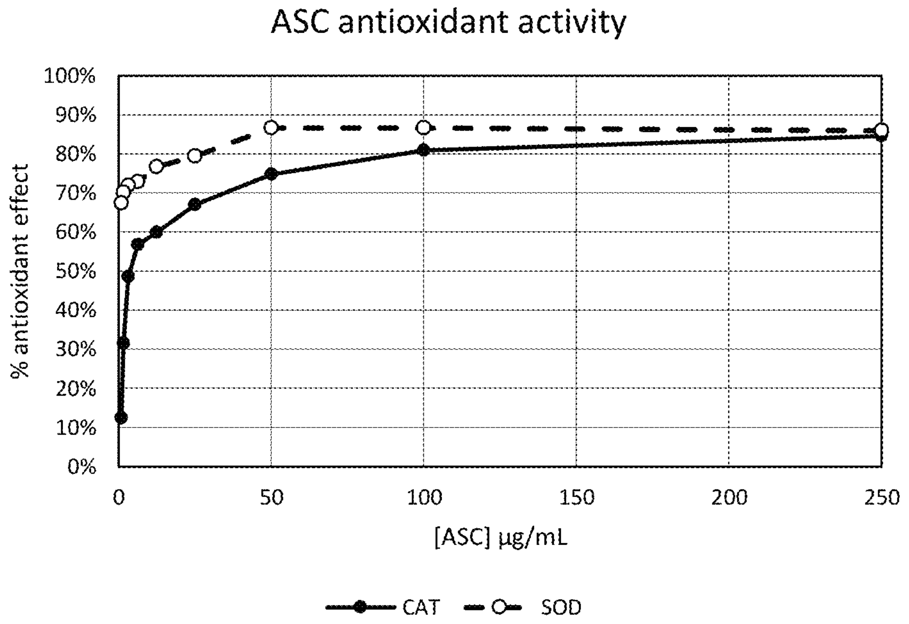
FIG. 13 shows a graph of reduction of activity of anti-oxidant enzymes from cells treated with an apple stem cell embodiment of the invention.

Results: Superoxide dismutase activity was measured in in vitro induced inflamed cells to determine the antioxidant effects of apple stem cell extracts at various concentration. The assay was performed in triplicate and the mean percent inhibition of SOD is present Table 7 and FIG. 13. The highest percent SOD inhibition was seen within groups treated with 50, 100 and 250 μg/mL ASC. The mean percentage SOD inhibition was noted to be 79.31, 81.74 and 84.3%, respectively. Statistically significant percent inhibition was observed in 100 and 250 μg/mL groups. The data suggest that the ASC can protect against oxidative damage in lung inflammation or stressed cells.

TABLE 24

Oxidation protection of ASC treated cells as measured by SOD assay. Reported values are means of triplicates ratioed to untreated cells.

| % SOD Inhibition Concentration (μg/mL) | Mean % | SD | SEM |
|---|---|---|---|
| 250 | 84.3 | 3.57 | 2.06 |
| 100 | 81.74 | 8.94 | 5.16 |
| 50 | 79.31 | 13.6 | 7.85 |
| 25 | 68.92 | 19.67 | 11.36 |
| 12.5 | 64.72 | 21.52 | 12.43 |
| 6.25 | 58.52 | 25.75 | 14.86 |
| 3.125 | 56.63 | 26.85 | 15.5 |
| 1.562 | 54.23 | 26.13 | 15.09 |
| 0.781 | 50.76 | 29.99 | 17.31 |

Results: Catalase. CAT activity was also measured in in vitro induced inflamed cells to determine the antioxidant potential of apple stem cell extracts at various concentration. The assay was performed in triplicate and the mean percent inhibition of CAT is present Table 8 and FIG. 14. The highest percent CAT inhibition was seen with the groups treated with 50, 100 and 250 μg/ml apple stem cell extract. The mean percentage CAT inhibition was noted to be 74.48, 80.73 and 84.38%, respectively with statistically significant percent inhibition recorded in 100 and 250 μg/ml groups (Table 25, FIG. 13). SOD and CAT data also suggest that the apple stem cell extracts can produce antioxidant activity in lung inflammation or stressed cells.

TABLE 25

Antioxidant activity of ASC treated cells as measured by CAT assay. Reported values are means of triplicates ratioed to untreated cells.

| % CAT Inhibition Concentration (μg/ml) | mean % | SD | SEM |
|---|---|---|---|
| 250 | 84.38 | 1.56 | 0.9 |
| 100 | 80.73 | 2.39 | 1.38 |
| 50 | 74.48 | 3.25 | 1.88 |
| 25 | 66.67 | 2.39 | 1.38 |
| 12.5 | 59.38 | 1.56 | 0.9 |
| 6.25 | 56.25 | 1.56 | 0.9 |
| 3.125 | 47.92 | 2.39 | 1.38 |
| 1.562 | 30.73 | 1.8 | 1.04 |
| 0.781 | 11.46 | 1.8 | 1.04 |

The results suggest apple stem cell extracts reduce SOD and CAT activity and thus may have value in treatment of pathologies including lung pathologies arising due to inflammatory responses. By reducing the elevation of anti-oxidant enzymes (presumably by directly reducing the level of ROS), the ASC treatment avoids both primary oxidative damage and the deleterious secondary consequences of enzyme elevation.

The embodiments described herein are referred in the specification as "one embodiment," "an embodiment," "an example embodiment," etc. These references indicate that the embodiment(s) described can include a particular feature, structure, or characteristic, but every embodiment does not necessarily include every described feature, structure, or characteristic. Further, when a particular feature, structure, or characteristic is described in connection with an embodiment, such feature, structure, or characteristic in may also be used in connection with other embodiments whether or not explicitly described. Further, where specific examples are given, the skilled practitioner may understand the particular examples as providing particular benefits such that the invention as illustratively disclosed herein suitably may be practiced in the absence of any element which is not specifically disclosed herein or within that particular example.

This disclosure mentions certain other documents incorporated by reference. Where such documents conflict with the express disclosure of this document, this document shall control.

It will be apparent to those of ordinary skill in the art that many modifications and variations of the described embodiment are possible in the light of the above teachings without departing from the principles and concepts of the disclosure as set forth in the claims.

Although the present disclosure describes certain exemplary embodiments, it is to be understood that such disclosure is purely illustrative and is not to be interpreted as limiting. Consequently, without departing from the spirit and scope of the disclosure, various alterations, modifications, and/or alternative applications of the disclosure will, no doubt, be suggested to those skilled in the art after having read the preceding disclosure. Accordingly, it is intended that the following claims be interpreted as encompassing all alterations, modifications, or alternative applications as fall within the true spirit and scope of the disclosure.

The invention claimed is:

1. A device for encouraging tissue regeneration in a respiratory system of a body, the device comprising:

a plant stem cell product having a regenerative effect, wherein the plant stem cell product comprises a plant stem cell derived from a plant selected from the group consisting of edible fruit-bearing angiosperms, seasoning herbs, spices, *Adhatoda vasica*, poppy, rose, hibiscus, mulberry, *cannabis*, coltsfoot, elecampane, *eucalyptus, Boswellia serrata*, hemp, *lebbeck*, lithy tree, licorice root, *Ocimum sanctum*, and mullein; and an aerosolizing device configured to apply an effective amount of the plant stem cell product to an injured area in the respiratory system.

2. The device of claim 1, wherein the plant stem cell product is derived from a dedifferentiated cell.

3. The device of claim 2, wherein the dedifferentiated cell includes a stem cell recovered from a part of a plant regenerating from an injury or the progeny of such a stem cell.

4. The device of claim 2, wherein the part of the plant includes one or more of a stem, a meristem, a leaf, a flower, a fruit, a seed, a root, or a callus.

5. The device of claim 1, wherein the plant stem cell product further includes an excipient.

6. The device of claim 5, wherein the excipient includes one or more of lactose, mannose, sodium chloride, a phospholipid, a poly lactic acid, poly (lactic-co-glycolic acid), glycerol, a glycol, a surfactant, a xanthan gum, or a liposome.

7. The device of claim 1, wherein the plant stem cell product is encapsulated.

8. The device of claim 1, wherein the plant stem cell product includes an extract of a plant stem cell encapsulated in a liposome comprising a phospholipid, glycerin, and xanthan gum.

9. The device of claim 1, wherein the aerosolizing device includes one or more of a nebulizer, pressurized metered-dose inhaler, a personal vaporizer, a humidifier, a powder inhaler, a personal diffuser, a traditional cigarette, or an electronic-cigarette.

10. The device of claim 1, wherein the aerosolizing device includes a smoking material, and wherein the plant stem cell product is applied to the smoking material.

11. The device of claim 1, wherein the plant stem cell product includes one or more of a plant stem cell extract, a lyophilized plant stem cell, a plant stem cell enriched medium, or an intact plant stem cell.

12. The device of claim 1, wherein the plant stem cell product is encapsulated in a capsule, and the capsule includes one or more of poly lactic acid, a poly (lactic-co-glycolic acid), a poly(methacrylate), or a liposome.

13. A method of encouraging tissue regeneration at a treatment site in a respiratory system of a mammal, the method comprising:

providing a plant stem cell product having a regenerative effect, wherein the plant stem cell product comprises a plant stem cell derived from a plant selected from the group consisting of edible fruit-bearing angiosperms, seasoning herbs, spices, *Adhatoda vasica*, poppy, rose, hibiscus, mulberry, *cannabis*, coltsfoot, elecampane, *eucalyptus, Boswellia serrata*, hemp, *lebbeck*, lithy tree, licorice root, *Ocimum sanctum*, and mullein;

providing an aerosolizing device;

delivering the plant stem cell product via the aerosolizing device into the respiratory system to apply an effective amount of the plant stem cell product to an injured area in the respiratory tract.

14. The method of claim 13, wherein the plant stem cell product includes one or more of a plant stem cell extract, a lyophilized plant stem cell, a plant stem cell enriched medium, or an intact plant stem cell.

15. The method of claim 13, wherein the delivery device includes one or more of a smoking material, a nebulizer, pressurized metered-dose inhaler, a personal vaporizer, a humidifier, a powder inhaler, a personal diffuser, a traditional cigarette, or an electronic-cigarette.

16. The method of claim 15, wherein the smoking material includes a smoking paper wrapped around an herb, wherein the step of delivering includes combusting the herb and inhaling smoke produced by the combustion.

17. The method of claim 15, wherein the plant stem cell product is encapsulated in a capsule that comprises a polymer or a liposome.

* * * * *